(12) United States Patent
Hazen et al.

(10) Patent No.: US 7,378,396 B2
(45) Date of Patent: May 27, 2008

(54) THERAPEUTIC AGENTS AND METHODS FOR CARDIOVASCULAR DISEASE

(75) Inventors: Stanley L. Hazen, Pepper Pike, OH (US); Marc S. Penn, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 11/198,005

(22) Filed: Aug. 5, 2005

(65) Prior Publication Data

US 2006/0074026 A1 Apr. 6, 2006

Related U.S. Application Data

(60) Provisional application No. 60/600,527, filed on Aug. 11, 2004, provisional application No. 60/600,551, filed on Aug. 11, 2004.

(51) Int. Cl.
*A61K 38/07* (2006.01)
*A61K 38/08* (2006.01)
*A61K 38/10* (2006.01)
*A61K 38/16* (2006.01)

(52) U.S. Cl. .................... 514/14; 514/13; 514/15; 514/16; 514/17; 514/18; 530/326; 530/327; 530/328; 530/329; 530/330

(58) Field of Classification Search .................. None
See application file for complete search history.

(56) References Cited

U.S. PATENT DOCUMENTS 5,122,534 A 6/1992 Loose et al.

(Continued)

FOREIGN PATENT DOCUMENTS

WO 01/38395 A1 5/2001

(Continued)

OTHER PUBLICATIONS

"Oxidized LDL and HDL: antagonists in atherothrombosis" by Mertens, et al., FASEB J., 15, 2073-2084 (2001).

(Continued)

*Primary Examiner*—Jeffrey Edwin Russel
(74) *Attorney, Agent, or Firm*—Calfee, Halter & Griswold LLP

(57) ABSTRACT

The present invention provides methods and agents for treating subjects who have or are at risk of developing or having cardiovascular disease. Such agents inhibit binding of myeloperoxidase (MPO) to a molecule comprising the MPO binding site of apolipoprotein A-1 (apoA-1) and include a peptide fragment of apoA-1 comprising at least 4 contiguous amino acids in SEQ ID. NO: 2, a modified form of the apo-1 fragment comprising one or more D amino acids, a retro-inverso form of the apoA-1 peptide fragment, an organo-mimetic of the apoA-1 peptide fragment, a peptide-mimetic of the apoA1 peptide fragment, or a nucleic acid encoding the apo A-1 peptide fragment. The present invention also provides methods of identifying or screening test agents for treating subjects having or at risk of having or developing CVD. The method comprises incubating one or more test agents and MPO with a molecule comprising the MPO binding site of apoA-1 under conditions which permit binding of MPO to the MPO binding site and determining whether one or more of the agents inhibit such binding.

11 Claims, 9 Drawing Sheets

U.S. PATENT DOCUMENTS

| | | | |
|---|---|---|---|
| 5,731,208 | A | 3/1998 | Heinecke |
| 5,747,274 | A | 5/1998 | Jackowski |
| 5,889,042 | A | 3/1999 | MacLean et al. |
| 5,962,636 | A * | 10/1999 | Bachmaier et al. ......... 530/326 |
| 5,985,272 | A | 11/1999 | Deby et al. |
| 6,040,147 | A | 3/2000 | Ridker et al. |
| 6,096,556 | A | 8/2000 | Heinecke |
| 6,133,039 | A | 10/2000 | Heinecke |
| 6,268,220 | B1 | 7/2001 | Heinecke |
| 6,953,666 | B1 | 10/2005 | Kinkade, Jr. et al. |
| 7,223,552 | B2 | 5/2007 | Hazen et al. |
| 2002/0156007 | A1 | 10/2002 | Graverson et al. |
| 2002/0164662 | A1 | 11/2002 | Hazen et al. |
| 2003/0008373 | A1 | 1/2003 | Bartel et al. |
| 2003/0045004 | A1 | 3/2003 | Barri et al. |
| 2003/0045460 | A1 | 3/2003 | Fogelman et al. |
| 2003/0119792 | A1 | 6/2003 | Roca |
| 2003/0180218 | A1 | 9/2003 | Hazen |
| 2004/0029807 | A9 | 2/2004 | Dasseux et al. |
| 2005/0202532 | A1 * | 9/2005 | Bielicki et al. ............ 435/69.1 |
| 2006/0051873 | A1 | 3/2006 | FitzGerald |
| 2006/0079475 | A1 * | 4/2006 | Zhang et al. .................. 514/44 |

FOREIGN PATENT DOCUMENTS

| | | |
|---|---|---|
| WO | 02/50550 A2 | 6/2002 |
| WO | 0248715 | 6/2002 |
| WO | 02062207 | 8/2002 |
| WO | 03/023397 A1 | 3/2003 |
| WO | WO 2005/061539 A2 * | 7/2005 |

OTHER PUBLICATIONS

"Macrophage scavenger receptor CD36 is the major receptor for LDL modified by monocyte-generated reactive nitrogen species" by Podrez, et al., J. Clin. Ivest. 105:1095-1108 (2000).

"Kinetics of Oxidation of Tyrosine and Dityrosine by Myeloperoxidase Compounds I and II" by Marquez, et al., The Journal of Biological Chemistry, vol. 270, No. 51, Dec. 22, 1995, pp. 30434-30440.

"Leukocytes Utilize Myeloperoxidase-Generated Nitrating Intermediates as Physiological Catalysts for the Generation of Biologically Active Oxidized Lipids and Sterols in Serum" by Schmitt, et al., Biochemistry, 1999, 38, 16904-16915.

"Nitric Oxide Modulates the Catalytic Activity of Myeloperoxidase" by Abu-Soud, et al., The Journal of Biological Chemistry, vol. 275, No. 8, Feb. 25, 2000, pp. 5425-5430.

"Mass spectrometric quantification of amino acid oxidation products in proteins: insights into pathways that promote LDL oxidation in the human artery wall" by Heinecke, et al., FASEB J., 13, 1113-1120 (1999).

"Myeloperoxidase-Generated Oxidants and Atherosclerosis" by Podrez, et al., Free Radical Biology & Medicine, vol. 28, No. 12, pp. 1717-1725, Jan. 2000.

"Myeloperoxidase, a Catalyst for Lipoprotein Oxidation, Is Expressed in Human Atherosclerosis Lesions" by Daugherty, et al., J. Clin. Invest., vol. 94, Jul. 1994, 437-444.

"3-Chlorotyrosine, a Specific Marker of Myeloperoxidase-catalyzed Oxidation, Is Markedly Elevated in Low Density Lipoprotein Isolated from Human Atherosclerosis Intima" by Hazen, et al., J. Clin. Invest., vol. 99, No. 9, May 1997, 2075-2081.

Elevated levels of protein-bound p-hydroxyphenylacetaldehyde, an amino acid-derived aldehyde generated by myeloperoxidase, are present in hun fatty streaks, intermediate lesions and advanced atherosclerosis lesions by Hazen, et al., Biochem J. (2000) 352, 693-699.

"p-Hydroxypheylacetaldehyde, an Aldehyde Generated by Myeloperoxidase, Modifies Phospholipid Amino Groups of Low Density Lipoprotein in Human Atherosclerosis Intima" by Heller, et al., The Journal of Biological Chemistry, vol. 275, No. 14, Apr. 7, 2000, pp. 9957-9962.

"Is the Oxidative Modification Hypothesis Relevant to Human Atherosclerosis? Do the Antioxidant Trials Conducted to Date Refute the Hypothesis?" by Steinberg, et al., Circulation, 2002; 105:2107-2111.

"Human Phagocytes Employ the Myeloperoxidase-Hydrogen Peroxide System to Synthesize Dityrosine, Trityrosine, Pulcherosine, and Isodityrosine by a Tyrosol Radical-dependent Pathway" by Jacob, et al., The Journal of Biological Chemistry, vol. 271, No. 33, Aug. 16, 1996, pp. 19950-19956.

"Kinetics of tryptophan oxidation in plasma lipoproteins by myeloperoxidase-generated HOCl" by Jerlich, et al., Eur. J. Biochem., 267, 4137-4143 (2000).

"Myeloperoxidase-generated reactive nitrogen species convert LDL into an atherogenic form in vitro" by Podrez, et al., The Journal of Clinical Investigation, Jun. 1999, vol. 103, No. 11, pp. 1547-1560.

"Formation of Nitric-Oxide Derived Oxidants by Myeloperoxidase in Monocytes, Pathways for Monocyte-Mediated Protein Nitration and Lipid Peroxidation In Vivo" by Hazen, et al., Circ Res. 1999; 85:950-958.

International Search Report Dated Oct. 12, 2005.

"Arg123-Tyr166 Domain of Human ApoA-1 Is Critical for HDL-Mediated Inhibition of Macrophage Homing and Early Atherosclerosis in Mice" by Holvoet, et al., Arterioscler Thromb Vasc Biol., Dec. 2001, pp. 1977-1983.

U.S. Appl. No. 10/972,058, filed Oct. 22, 2004, entitled: Assessing the Risk of a Major Cardiac Event in Patients with Chest Pain.

U.S. Appl. No. 10/417,838, filed Apr. 17, 2003, entitled: Systemic Marker for Monitoring Anti-Inflammatory and Antioxidant Actions of Therapeutic Agents.

U.S. Appl. No. 11/412,065, filed Apr. 26, 2006, entitled: Systemic Marker for Monitoring Anti-Inflammatory and Antioxidant Actions of Therapeutic Agents.

U.S. Appl. No. 11/313,012, filed Dec. 20, 2005, entitled: Myeloperoxidase, A Risk Indicator for Cardiovascular Disease.

U.S. Appl. No. 11/005,563, filed Dec. 6, 2004, entitled: Risk Markers for Cardiovascular Disease.

Office Action dated Mar. 21, 2007, for U.S. Appl. No. 11/005,563, filed Dec. 6, 2004, entitled: Risk Markers for Cardiovascular Disease.

Supplementary Partial European Search Report dated May 31, 2007.

"Association of Nitrotyrosine Levels With Cardiovascular Disease and Modulation by Statin Therapy" by Shishehbor, et al., JAMA 2003;289:1675-1680.

"Associations between change in C-reactive protein and serum lipids during statin treatment" by Strandberg, et al., Ann Med 2000;32:579-583.

"Effects of Low Doses of Simvastatin and Atrovastatin on High-Density Lipoprotein Cholesterol Levels in Patients with Hypercholesterolemia" by Branchi, et al., Clinical Therapeutics, vol. 23, No. 6, 2001, pp. 851-857.

"Modification of Proteins and Lipids by Myeloperoxidase" by Hazen, et al., Methods in Enzymology, vol. 300, pp. 89-105. (1999).

"Mechanisms of oxidative damage by myeloperoxidase in atherosclerosis and other inflammatory disorders" by Heinecke, J Lab Clin Med 1999;133:321-5.

"The Oxidative Modification Hypothesis of Atherogenesis: An Overview" by Chisolm, et al., Free Radical Biology & Medicine, vol. 28, No. 12, pp. 1815-1826, 2000.

"Myeloperoxidase binds to low-denisity lipoprotein: potential implications for atherosclerosis" by Carr, et al., FEBS Letters, 487 (2000) 176-180.

Abstract: "Elevated Levels of Plasma Myeloperoxidase, an Oxidative Enzyme Degranulated from Activated Phagocytes, in Patients with Coronary Artery Disease and Acute Coronary Syndromes" by Sugiyama, et al., Circulation, vol. 106, No. 19, Nov. 5, 2002, p. 2637.

"Myeloperoxidase Serum Levels Predict Risk in Patients With Acute Coronary Syndromes" by Baldus, et al., Circulation, 2003;108:1440-1445.

"Intracellular Neutrophil Myeloperoxidase Is Reduced in Unstable Angina and Acute Myocardial Infarction, but its Reduction is Not Related to Ischemia" by Biasucci, et al., J Am Coll Cardiol 1996;27:611-6).

"Defects in leukocyte-mediated initiation of lipid peroxidation in plasma as studied in myeloperoxidase-deficient subjects: systematic identification of multiple endogenous diffusible substrates for myeloperoxidase in plasma" by Zhang, et al., Blood, 2002;99:1802-1810.

"Thrombosis and Acute Coronary-Artery Lesions in Sudden Cardiac Ischemic Death" by Davies, et al., N Engl J Med 1984;310:1137-40.

"Increased Neutrophil Elastase Release in Unstable Angina Pectoris and Acute Myocardial Infarction" by Dinerman, et al., J Am Coll Cardiol 1990;15:1559-63.

"Neutrophil Infiltration of Culprit Lesions in Acute Coronary Syndromes" by Naruko, et al., Circulation, 2002;106:2894-2900.

"Widespread Coronary Inflammation in Unstable Angina" by Buffon, et al., N Engl J Med 2002;347:5-12.

"Myeloperoxidase Functions as a Major Enzymatic Catalyst for Initiation of Lipid Peroxidation at Sites of Inflammation" by Zhang, et al., The Journal of Biological Chemistry, vol. 277, No. 48, Nov. 29, 2002, pp. 46116-46122.

"The Effect of Local Attachment of Cationized Antioxidant Enzymes on Experimental Colitis in the Rat" by Blau, et al., Pharmaceutica Research, vol. 17, No. 9, 2000, pp. 1077-1084.

"Intestinal anti-infammatory activity of morin on chronic experimental colitis in the rat" by Galves, et al., Aliment Pharmacol Ther 2001;15:2027-2039.

"Effects of Morin on an Experimental Model of Acute Colitis in Rats" by Ocete, et al., Pharmacology 1998;57:261-270.

"Protective effect of melatonin in a non-septic shock model induced by zymosan in the rat" by Cuzzacrea, et al., J Pineal Res 1998;25:24-33.

"Antinflammatory Effects of Cordia myxa Fruit on Experimentally Induced Colitis in Rats" by Al-Awadi, et al., Nutrition 2001;17:394-396.

"Efficacy of use of colonoscopy in dextran sulfate sodium induced ulcerative colitis in rats: the evaluation of the effects of antioxidant by colonoscopy" by Ahn, et al., Int J Colorectal Dis (2001) 16:174-181.

"Taurine Can Ameliorate Inflammatory Bowel Disease in Rats" by Son, et al., Taurine 3, edited by Schaffer, et al., Plenum Press, New York, 1998.

"Simvastatin ameliorates injury in an experimental model of lung ischemia-reperfusion" by Naidu, et al., J Thorac Cardiovasc Surg 2003;126:482-9.

"Protective Effect of Famotidine, Omeprazole, and Melatonin Against Acetylsalicylic Acid-Induced Gastric Damage in Rats" by Sener-Muratoglu, et al., Digestive Diseases and Sciences, vol. 46, No. 2 (Feb. 2001), pp. 318-330.

"Primary Prevention of Acute Coronary Events with Lovastatin in Men and Women with Average Cholesterol Levels" by Downs, et al., JAMA, 1998;279:1615-1622.

"The Effect of Pravastatin on Coronary Events After Myocardial Infarction in Patients with Average Cholesterol Levels" by Sacks, et al., N Engl J Med 1996;335:1001-9.

"Beyond Cholesterol: Modifcations of Low-Density Lipoprotein That Increase Its Atherogenicity" by Steinberg, et al., N Engl J Med 1989;320:915-924.

"Pieiotropic Effects on 3-Hydroxy-3-Methylglutaryl Coenzyme A Reductase Inhibitors" by Takemoto, et al., Aterioscler Thormb Vasc Biol. 2001;21:1712-1719.

"The Evolving Role of Statins in the Management of Atherosclerosis" by Vaughan, et al., J Am Coll Cardiol 2000;35:1-10.

"Reduction of Plasma 24S-Hydroxycholesterol (Cerebrosterol) Levels Using High-Dosage Simvastatin in Patients with Hypercholesterolemia" by Locatelli, et al., Arch Neurol. 2002;59:213-216.

"Alzheimer's Disease: Bad for the Heart, Bad for the Mind?" by Marx, Science, 2001;294:508-509.

"3-Hydroxy-3-methylglutaryl-coenzyme A reductase mRNA in Alzheimer and control brain" by Yasojima, et al., NeuroReport 2001; 12:2935-2938.

"Lovastatin Treatment Decreases Mononuclear Cell Infiltration Into the CNS of Lewis Rats with Experimental Allergic Encephalomyelitis" by Stanislaus, et al., J Neurosci Res 66:155-162, 2001.

"Effect of Hydroxymethylglutaryl Coenzyme A Reductase Inhibitors on the Progression of Cacific Aortic Stenosis" by Navaro, et al., Circulation, 2001;104:2205-2209.

"Measurement of C-Reactive Protein for the Targeting of Statin Therapy in the Primary Prevention of Acute Coronary Events" by Ridker, et al., N Engl J Med 2001;344:1959-65.

"Rapid Reduction in C-Reactive Protein with Cerivastatin Among 785 Patients with Primary Hypercholesterolemia" by Ridker, et al., Circulation, 2001;103:1191-1193.

"Are Statins Anti-Inflammatory? Issues in the Design and Conduct of the Pravastatin Inflammation C-Reactive Protein Evaluation" by Ridker, et al., Current Cardiology Reports, 2000;2:269-2730.

International Search Report dated Jul. 31, 2002.

"Inhibition of Adhesion Molecules Markedly Ameliorates Cytokine-Induced Sustained Myocardial Dysfunction in Dogs in vivo" by Momii, et al., J Mol Cell Cardiol 30, 2637-2650 (1998).

"Supplementation with Tetrahydrobiopterin Suppresses the Development of Hypertension in Spontaneously Hypertensive Rats" by Hong, et al., Hypertension, 2001;38:1044-1048.

Supplementary European Search Report dated Jan. 29, 2004.

"Circulating Myeloperoxidase and Anti-Myeloperoxidase Antibody in Patients with Vasculitis" by Minota, et al., Scand J Rheumatol 1999;28:94-9.

"Myeloperoxidase Deficiency" by Nauseef, et al., Hematology/Oncology Clinics of North America, vol. 2, No. 1, Mar. 1988, pp. 135-158.

"Primary Inherited Defects in Neutrophil Function: Etiology and Treatment" by Malech, et al., Seminars in Hematology, vol. 34, No. 4 Oct. 1997: pp. 279-290.

"Association Between Myeloperoxidase Levels and Risk of Coronary Artery Disease" by Zhang, et al., JAMA, 2001;286:2136-2142.

Abstract: "Lovastatin Inhibits Low-Density Lipoprotein Oxidation and Alters its Fluidity and Uptake by Macrophages: in vitro and in vivo studies" by Aviram, et al., Metabolism, Clinical and Experimental (1992), 41(3), 229-35.

"Plasma sialic acid and coronary artery atheromatous load in patients with stable chest pain" by Wu, et al., Atherosclerosis 145 (1999) 261-266.

Webster's II New Riverside Dictionary (See p. 1013; 1994 Riverside Publishing Company).

International Search Report dated Nov. 27, 2007.

"Apolipoprotein A-1 is a selective target for myeloperoxidase-catalyzed oxidation and functional impairment in subjects with cardiovascular disease" by Zheng, et al., J. Clin. Invest. 114:529-541 (2004).

* cited by examiner

THERAPEUTIC AGENTS AND METHODS FOR CARDIOVASCULAR DISEASE

PRIORITY CLAIM

This application claims priority to U.S. Provisional Application No. 60/600,527 filed Aug. 11, 2004 and U.S. Provisional application No. 60/600,551, filed Aug. 11, 2004, both of which are incorporated herein by reference in their entirety.

GOVERNMENT SUPPORT

This work was supported by National Institutes of Health grants P01 HL076491 and HL70621. The government has certain rights in this invention.

FIELD OF THE INVENTION

The present invention relates to the field of cardiovascular disease. More specifically, it relates to therapeutic agents for treating subjects with cardiovascular disease or at risk of having or developing cardiovascular disease and methods for identifying therapeutic agents for cardiovascular disease.

BACKGROUND

Cardiovascular disease (CVD) is the general term for heart and blood vessel diseases, including atherosclerosis, coronary heart disease, cerebrovascular disease, aorto-iliac disease, and peripheral vascular disease. Subjects with CVD may develop a number of complications, including, but not limited to, myocardial infarction, stroke, angina pectoris, transient ischemic attacks, congestive heart failure, aortic aneurysm and death. CVD accounts for one in every two deaths in the United States and is the number one killer disease. Thus, prevention of cardiovascular disease is an area of major public health importance.

Currently, several risk factors are used by medical professionals to assess an individual's risk of developing or having CVD and to identify individuals at high risk. Major risk factors for cardiovascular disease include age, hypertension, family history of premature CVD, smoking, high total cholesterol, low HDL cholesterol, obesity and diabetes, C-reactive protein, blood levels of myeloperoxidase (See commonly assigned U.S. patent application Ser. No. 10/039,753, which is specifically incorporated herein by reference in its entirety) or modified apolipoprotein A-1 (See commonly assigned, U.S. application Ser. No. 11/005,563, which is specifically incorporated herein by reference in its entirety.) The major risk factors for CVD are typically used together by physicians in a risk prediction algorithm to target those individuals who are most likely to benefit from treatment for CVD. In addition, CVD can develop and CVD complications can occur in individuals with apparently low to moderate risk profiles, as determined using currently known risk factors.

A low-fat diet and exercise are recommended to prevent CVD. In addition, a number of therapeutic agents may be prescribed by medical professionals to those individuals who are known to be at risk for developing or having CVD. These include lipid-lowering agents that reduce blood levels of cholesterol and trigylcerides, agents that normalize blood pressure, agents, such as aspirin or platelet ADP receptor antatoginist (e.g., clopidogrel and ticlopidine), that prevent activation of platelets and decrease vascular inflammation, and pleotrophic agents such as peroxisome proliferator activated receptor (PPAR) agonists, with broad-ranging metabolic effects that reduce inflammation, promote insulin sensitization, improve vascular function, and correct lipid abnormalities. More aggressive therapy, such as administration of multiple medications or surgical intervention may be used in those individuals who are at high risk. Since CVD therapies may have adverse side effects, it is desirable to have additional agents for treating individuals who have or are at risk of having or developing CVD.

SUMMARY OF THE INVENTION

The present invention provides methods and agents for treating subjects at risk of developing or having cardiovascular disease. Such agents inhibit binding of myeloperoxidase (MPO) to a molecule comprising the MPO binding site of apolipoprotein A-1 (Apo A-1). The present invention is based, at least in part, on the discoveries that a) apoA-1 is the preferred target for nitration and chlorination in serum, b) MPO and apoA-1 can be co-precipitated from plasma using an anti-MPO antibody, c) MPO preferentially binds to a peptide comprising A190-L203 of apoA-1, d) MPO generated reactive halogen and reactive nitrogen species modify apoA-1, the major lipoprotein of HDL, and inhibit ABCA1-dependent cholesterol efflux functions of apo A-1 and HDL, and d) peptides comprising L amino acids or D amino acids and the sequence AEYHAKATEHLSTL, SEQ ID NO: 2 block binding of MPO to apoA1 and HDL. In accordance with the present invention, the agents, referred to hereinafter collectively as apoA1-MPO Binding Inhibitors (AMBI), include peptides, peptide mimetics of such peptides, and small molecule organo-mimetics of such peptides. The present therapeutic agents also include nucleic acids that encode the present inhibitor peptides. The apoA1-MPO binding inhibitors of the present invention can be incorporated into pharmaceutical compositions and used to treat subjects who are diagnosed as having or who are at risk of having or developing CVD The present invention also provides methods of treating subjects having or at risk of having or developing CVD. The method comprises administering a therapeutically effective amount of one or a combination of the apoA1-MPO binding inhibitors. In certain embodiments, an AMBI and a second therapeutic agent for treating CVD are administered to the subject.

The present invention also provides methods of identifying or screening test agents for treating subjects having or at risk of having or developing CVD. The method comprises incubating one or more test agents with MPO and a molecule comprising the MPO binding site of apoA-1 under conditions which permit binding of MPO to the MPO binding site, and determining whether one or more of the agents inhibit such binding. A test agent that inhibits such binding is expected to be useful for treating subjects with CVD or at risk of having or developing CVD. In certain embodiments, the inhibitory activity of the test agent is compared to the inhibitory activity of a 4-14 amino acid peptide that comprises 4 to 14 consecutive amino acids in the sequence AEYHAKATEHLSTL, SEQ ID NO:2, or from 4 to 14 consecutive amino acids in the sequence LTSLHETAKAHYEA, SEQ ID NO: 3.

DETAILED DESCRIPTION OF THE INVENTION

Figure 1:
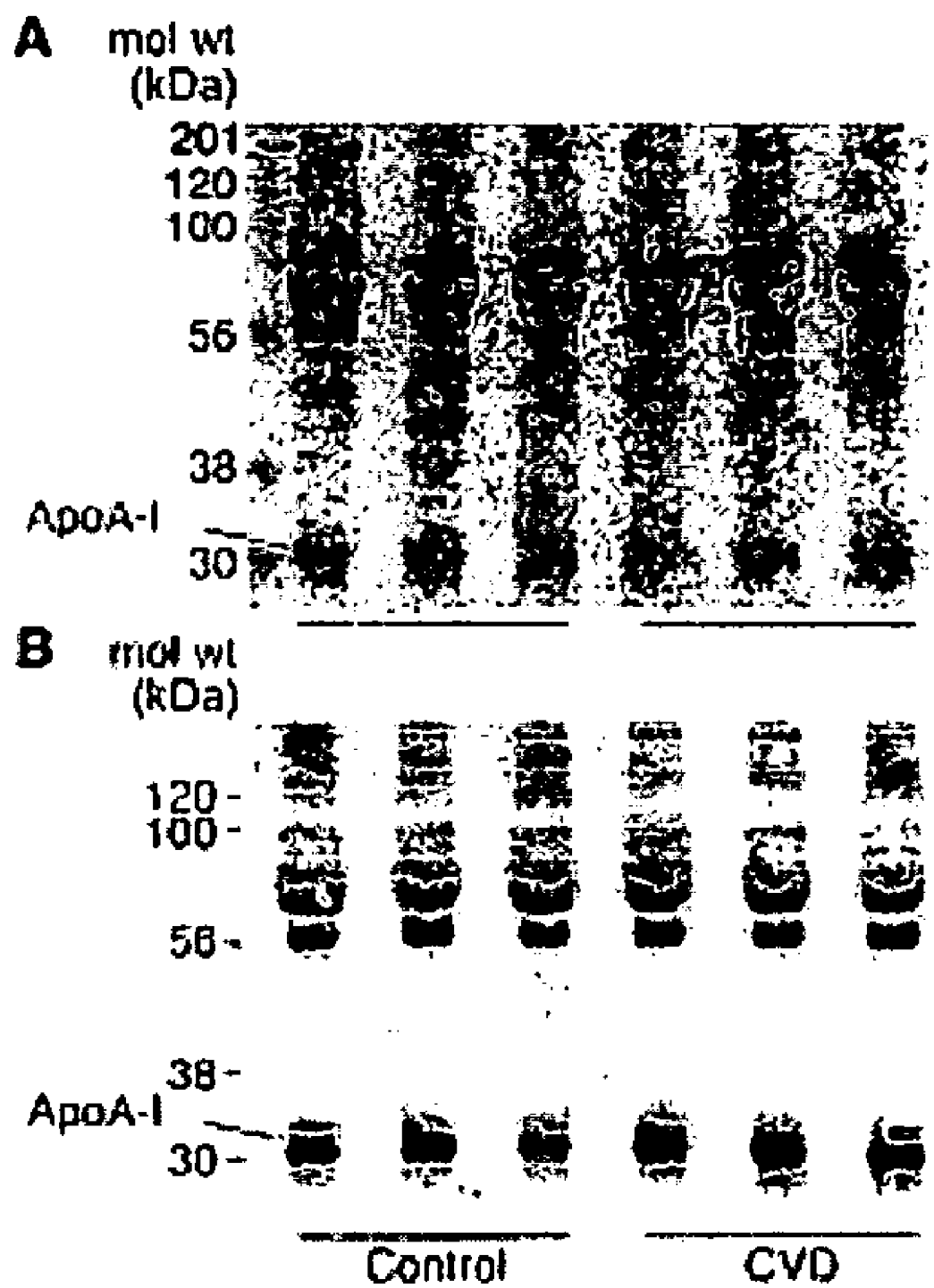
FIG. 1. Apolipoprotein A-I is a preferred target for nitration in serum. Serum samples (25 μg total protein per lane) from 3 healthy controls and 3 subjects with cardiovascular disease were separated by SDS-PAGE. The gels (12.5%) were either (Bottom) transferred and probed with a monoclonal antibody specific for protein-bound nitrotyrosine or (Top) stained for protein with Coomassie blue. The apoA-I bands were identified by sequence analysis by tandem mass spectrometry. The disproportionate recognition of the apoA-I band in the Western blot analysis is consistent with an enhanced nitrotyrosine content of that protein.

The present invention will now be described by reference to more detailed embodiments, with occasional reference to the accompanying drawings. This invention may, however, be embodied in different forms and should not be construed as limited to the embodiments set forth herein. Rather these embodiments are provided so that this disclosure will be thorough and complete, and will convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

All publications, patent applications, patents, and other references mentioned herein are incorporated by reference in their entirety.

Definitions.

The term "apoA-1 peptide fragment" as used herein refers to a peptide that comprises fewer amino acids than the full-length apoA-1.

The term "treating" when used with respect to "treating" a subject with cardiovascular disease or at risk of having or developing cardiovascular disease refers to a reduction, prevention, or elimination of one or more symptoms, complications, or manifestations characteristic of a cardiovascular disease. Such a reduction includes, but is not limited to, a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like. "Treating one or more symptoms of cardiovascular disease" can also refer to improving blood flow to vascular beds affected by a cardiovascular disease.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "purified" as used herein does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50%, preferably at least 75%, more preferably at least 90% of the total peptide or protein content of the preparation.

Dysfunctional Forms of HDL

Despite the consistent demonstration that a low plasma HDL is a strong predictor of clinical risk, it is apparent that many patients with 'normal' or even 'elevated' plasma HDL experience clinical events. In fact, nearly half of the clinical events in the Framingham cohort occurred in subjects with plasma HDL concentrations ≧40 mg/dl (Kwiterovich P O, Jr: 1998. Am J Cardiol 82:13Q-21Q.). It has been proposed that HDL with impaired functional properties within subjects of this cohort may lead to either a loss of protective benefit or even an actual promotion of atherogenic events (Ansell B J, Navab M, Hama S, et al.: 2003. Circulation 108:2751-2756.).

It is therefore of interest that HDL recovered from different subjects often demonstrates marked heterogeneity in its in vitro functional properties. For example, Ashby and colleagues demonstrated that HDL isolated from distinct subjects differed markedly in their ability to inhibit cytokine induced expression of the adhesion molecule vascular cell adhesion molecule-1 (VCAM-1) by endothelial cells (Ashby D T, Gamble J R, Vadas Mass., et al.: 2001. Atherosclerosis 154:113-121). Several investigators have similarly reported that HDL isolated from diabetic subjects has impaired ability both to promote cellular cholesterol efflux and to prevent the oxidation of LDL (Gowri M S, Van der Westhuyzen D R, Bridges S R, et al.: 1999. Arterioscler Thromb Vasc Biol 19:2226-2233; Syvanne M, Castro G, Dengremont C, et al.: 1996. Atherosclerosis 127:245-253.).

Another intriguing observation is that the anti-inflammatory properties of HDL reportedly decline in the setting of the acute phase response. Van Lenten and colleagues compared the functional properties of HDL isolated from subjects before versus following elective surgery (Van Lenten B J, Hama S Y, de Beer F C, et al.: 1995. J Clin Invest 96:2758-2767.). HDL isolated preoperatively demonstrated anti-inflammatory properties, such as the ability to inhibit LDL oxidation and subsequent monoctye chemotaxis. In contrast, HDL isolated postoperatively promoted both LDL oxidation and monocyte chemotaxis. Functional properties of HDL during acute phase responses have been further studied in humans, rabbits and mice (Ashby et al. 2001; Van Lenten et al. 1995; Van Lenten B J, Wagner A C, Nayak D P, et al.: 2001. Circulation 103:2283-2288.). The transition to a pro-inflammatory form of HDL is reportedly associated with alterations in the composition of circulating HDL-associated proteins. Both reductions in the HDL contents of paraoxonase and platelet activating factor acetylhydrolase, as well as parallel elevations in HDL content of serum amyloid A and ceruloplasmin, are reported (Van Lenten et al. 1995). These alterations in composition may underscore the observed effects of such "pro-inflammatory" HDL on monocyte chemotaxis (Ansell et al. 2003). Of interest, six weeks of treatment with simvastatin reportedly reduced the extent of monocyte chemotaxis induced by HDL preparations isolated from subjects with prior pro-inflammatory HDL (Ansell et al. 2003). These results further support the notion that the quality, rather than quantity, of circulating HDL may serve as the more important determinant of overall cardiovascular risk.

The present invention provides agents and methods for treating subjects at risk of developing or having cardiovascular disease. Such agents inhibit binding of MPO to HDL and apoA-1, and include peptides, peptide mimetics of the present peptides and small molecule organo-mimetics of the present peptides. The present therapeutic agents also include nucleic acids that encode the present inhibitor peptides.

Peptides, Peptide Mimetics, and Organo-Mimetics for Treating Patients Having or at Risk or Having or Devoloping CVD In one embodiment the AMBI is an apoA-1 peptide fragment that comprises at least 4 contiguous amino acids within the myeloperoxidase ("MPO") binding site of apoA-1, a modified form of such peptide fragment that comprises one or more dexorotary (D) amino acids, or a retro-inverso isomer of such peptide fragment. The AMBI may also be a peptide mimetic or small molecule organo-mimetic which supports the same binding activity to the MPO binding site of apo A-1 as the apoA-1 peptide fragment. The ABMI binds MPO with an affinity which is equivalent to the affinity of HDL for this enzyme. This property can be determined empirically using a competitive binding analysis. Alternatively, the relative affinity of the ABMI for MPO can be estimated on the basis of Ka and Kd measurements.

In certain embodiments, the AMBI is a peptide fragment of ApoA-1 that is from 4 to 14 amino acids in length that comprises at least 4 consecutive amino acids in A190-L203 of SEQ ID NO: 1. Thus, in certain embodiments, the AMBI is a peptide that is 4, 5, 6, 7, 8, 9, 10, 11, 12, 13 or 14 amino acids in length, and that, respectively comprises 4, 5, 6, 7, 8, 9, 10, 11, 12, 13, or 14 consecutive amino acids in the sequence AEYHAKATEHLSTL, SEQ ID NO:2. In other embodiments, the peptide is a modifed apoA-1 peptide fragment, that comprises one or more D amino acids and a consecutive sequence of from 4, 5, 6, 7, 8, 9, 10, 11, 12, 13, or 14 amino acids in the sequence AEYHAKATEHLSTL, SEQ ID NO:2. The D-form amino acids can be incorporated at any position in the peptide as desired. Thus, for example, in one embodiment, the peptide can comprise a single D-amino acid, while in other embodiments, the peptide can comprise 2, 3, 4, 5, 6, 7, 8, 9, 10, 11, 12, 13, 14 or more D amino acids. Thus, in one embodiment, the peptide is 14 amino acids in length, formed entirely of D amino acids and has the sequence set forth in SEQ ID NO:2. In other embodiments, the peptide is a retro inverso isomer of the apoA-1 peptide fragment and comprises 4, 5, 6, 7, 8, 9, 10, 11, 12, 13, or 14 D amino acids in the sequence LTSLHE-TAKAHYEA, SEQ ID NO:3. The terms "D amino acid" and "L amino acid" are used to refer to absolute configuration of the amino acid, rather than a particular direction of rotation of plane-polarized light. The usage herein is consistent with standard usage by those of skill in the art. In other embodiments, the AMBI is a purified peptide fragment of apoA1 that comprises at its (i.e. at the fragment's) amino terminus amino acids 199-203 of mature apo A-1, i.e., the apo A1 protein that lacks a signal sequence, i.e., SEQ ID NO.1. In other embodiments, the AMBI is a purified peptide fragment of apo A1 that comprises at its (i.e., at the fragment's) carboxy terminus amino acids 190-193-of mature apo A1, i.e. SEQ ID NO.1.

In certain instances, the peptide, referred to hereinafter as "L" peptide, comprises all levorotary amino acids. In other instances the peptide, referred to hereinafter as a "D" peptide, comprises all dexorotary amino acids such that the D peptide mimetic is a topochemical equivalent of the corresponding L peptide. The dextro retro-inverso modification of the L-peptide produces a corresponding D peptide that also involves the reversal of all amide bonds within the peptide backbone. This is achieved by reversing the direction of sequence and inverting the chirality of each amino acid residue by using D-amino acids. The goal of this topochemical approach is to create an analog such that the reversed amide bonds in the dextro retroinverso peptide retains both the planarity and conformational restrictions of peptide bonds (CONH) and the spatial orientation of side chains remains closely related to that of the corresponding L peptide. The D peptide simply retains the peptide sequence with each amino acid possessing the inverse chirality of each amino acid relative to the L (levo) peptide. Advantageously, D peptides are resistant to proteases that are present in mammals. In other embodiments, the peptide comprises both L and D amino acids. Either one or both of the amino and carboxy termini of the AMBI peptide may be free or, preferably, end-blocked.

Peptide forms of the AMBI may be a polymer of naturally-occurring amino acids that may be linear or branched. They may also be assembled into a complex of more than one polypeptide chain. The AMBI may be a peptide that also encompasses amino acid polymers that have been modified, such as by disulfide bond formation. The AMBI includes peptides that comprise non-sequence modifications, e.g. glycosylation, lipidation, acetylation, phosphorylation, pegylation, carboxylation, methylation, or any other manipulation or modification, such as conjugation with a labeling component. While, in preferred embodiments, the peptides of this invention utilize naturally-occurring amino acids or D isoforms of naturally occurring amino acids, substitutions with non-naturally occurring amino acids (e.g., methionine sulfoxide, methionine methylsulfonium, norleucine, epsilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl) or synthetic analogs, e.g. .alpha.-aminoisobutyric acid, .beta. or .gamma.-amino acids; and cyclic analogs. In another embodiment, AMBI is a fusion protein that comprises a first moiety which is a peptide of the present invention and a second moiety which is a heterologous peptide.

Peptides of the present invention may be modified by a variety of chemical techniques to produce derivatives having essentially the same activity as the unmodified peptides, and optionally having other desirable properties. For example, carboxylic acid groups of the peptide, whether carboxyl-terminal or side chain, may be provided in the form of a salt of a pharmaceutically-acceptable cation or esterified to form a $C1-C_{16}$ ester, or converted to an amide of formula $NR_1R_2$ wherein $R_1$ and $R_2$ are each independently H or $C1-C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C1-C_{16}$ alkyl or dialkyl amino or further converted to an amide.

Hydroxyl groups of the peptide side chain may be converted to $C1-C_{16}$ alkoxy or to a $C_1-C_{16}$ ester using well-recognized techniques. Phenyl and phenolic rings of the peptide side chain may be substituted with one or more halogen atoms, such as fluorine, chlorine, bromine or iodine, or with $C_1-C_{16}$ alkyl, $C_1-C_{16}$ alkoxy, carboxylic acids and esters thereof, or amides of such carboxylic acids. Methylene groups of the peptide side chains can be extended to homologous $C_2-C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Additionally, while specific reference is made to discrete peptides, polypeptides, and/or proteins, mutants or variants of those peptides or proteins are specifically contemplated as well. A "variant" as used herein, refers to a peptide or polypeptide whose amino acid sequence is similar to a reference peptide/polypeptide, but does not have 100% identity to the reference peptide/polypeptide sequence. A variant peptide/polypeptide has an altered sequence in which one or more of the amino acids in the reference sequence is deleted or substituted, or one or more amino acids are inserted into the sequence of the reference amino acid sequence, e.g. SEQ ID NO:2. A variant can have any combination of deletions, substitutions, or insertions. As a result of the alterations, a variant peptide/polypeptide can have an amino acid sequence which is at least about 80, 81, 82, 83, 84, 85, 86, 87, 88, 89, 90, 91, 92, 93, 94, 95, 96, 97, 98, 99, or higher percent, identical to the reference sequence. Variants can be prepared using any suitable method, (e.g., solid phase peptide synthesis, by expression of nucleic acids encoding the variant), and tested for their ability to inhibit binding of MPO to HDL, apo A-1 or the MPO-binding site of apo A-1. These sorts of variants, which may or may not be naturally occurring, are expressly contemplated.

Sequence identity is frequently measured in terms of percentage identity between two aligned sequences. Methods of alignment of sequences for comparison are well-known in the art. Various programs and alignment algorithms are described in: Smith and Waterman, Adv. Appl. Math. 2:482, 1981; Needleman and Wunsch, J. Mol. Bio. 48:443, 1970; Pearson and Lipman, Methods in Molec. Biology 24: 307-331, 1988; Higgins and Sharp, Gene 73:237-244, 1988; Higgins and Sharp, CABIOS 5:151-153, 1989; Corpet et al., Nucleic Acids Research 16:10881-90, 1988; Huang et al., Computer Applications in BioSciences 8:15 5-65,1992; and Pearson et al., Methods in Molecular Biology 24:307-31,1994. Altschul et al. (1994) presents a detailed consideration of sequence alignment methods and homology calculations.

The NCBI Basic Local Alignment Search Tool (BLAST) (Altschul et al., J. Mol. Biol. 215:403-410, 1990) is available from several sources, including the National Center for Biological Information (NBCI, Bethesda, Md.) and on the Internet, for use in connection with the sequence analysis programs blastp, blastn, blastx, tblastn and tblastx.

In order to maintain an optimally functional peptide, particular peptide variants will differ by only a small number of amino acids from the peptides disclosed in this specification. Such variants may have deletions (for example of 1, 2 or more amino acid residues), insertions (for example of 1, 2 or more residues), or substitutions that do not interfere with the desired inhibitory activity of the peptides. Substitutional variants are those in which at least one residue in the amino acid sequence has been removed and a different residue inserted in its place. In particular embodiments, such variants will have amino acid substitutions of single residues. Such substitutions generally are made in accordance with the following Table 1 when it is desired to finely modulate the characteristics of the peptide.

TABLE 1

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Greater changes in biological activity may be made by selecting substitutions that are less conservative than those in Table 1, i.e. selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., Bio Technique 1: 11-15 (1989)), or saturation mutagenesis (by, e.g., chemical treatment or irradiation of single-stranded DNA in vitro, and synthesis of a complementary DNA strand; Mayers et al., Science 229: 242 (1985)). Random mutagenesis can also be accomplished by, e.g., degenerate oligonucleotide generation (using, e.g., an automatic DNA synthesizer to chemically synthesize degenerate sequences; Narang, Tetrahedron 39: 3 (1983); Itakura et al., Recombinant DNA, Proc. 3rd Cleveland Sympos. Macromolecules, ed. A. G. Walton, Amsterdam: Elsevier, pp. 273-289 (1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above. Methods for identifying desirable mutations include, e.g., alanine scanning mutagenesis (Cunningham and Wells, Science 244: 1081-1085 (1989)), oligonucleotide-mediated mutagenesis (Adelman et al., DNA, 2: 183 (1983)); cassette mutagenesis (Wells et al., Gene 34: 315 (1985)), combinatorial mutagenesis, and phage display libraries (Ladner et al., PCT International Appln. No. WO88/06630). The variants can be tested, e.g., for their ability to reduce or inhibit binding of MPO to apoA1 as described herein In certain embodiments, one or more R-groups on the constituent amino acids and/or the terminal amino acids of the AMBI peptide are blocked with a protecting group. A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain embodiments, the protecting groups include, but are not limited to alkyl chains as in fatty acids, propeonyl, formyl, and others. In certain embodiments, an acetyl group is used to protect the amino terminus and an amide group is used to protect the carboxyl terminus. In certain particularly preferred embodiments, the protecting groups include, but are not limited to alkyl chains as in fatty acids, propeonyl, formyl, and others. Particularly preferred carboxylprotecting groups include amides, esters, and ether-forming protecting groups. Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylid-ene)ethyl (Dde), 2,6-dichlorobenzyl (2,6-DiCl-Bzl), 2-chlorobenzyloxycarbonyl (2-Cl—Z), 2-bromobenzyloxycarbonyl (2—Br-Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

In addition to peptides, small molecule organo-mimetics and peptidomimetics of the present peptides are also contemplated herein. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) Adv. Drug Res. 15: 29; Veber and Freidinger (1985) TINS p. 392; and Evans et al. (1987) J. Med. Chem. 30: 1229) and are usually developed with the aid of computerized molecular modeling. Peptide mimetics that are structurally similar to therapeutically useful peptides may be used to produce an equivalent therapeutic or prophylactic effect.

The three-dimensional arrangement of the chemical constituents of such peptide mimetics and organo-mimetics mimic the three-dimensional arrangement of the peptide backbone and component amino acid side chains in the peptide, resulting in such peptide mimetics and organo-mimetics having substantial specific inhibitory activity. For computer modeling applications, a pharmacophore is an idealized, three-dimensional definition of the structural requirements for biological activity. Peptide mimetics and organo-mimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and Principles of Pharmacology (ed. Munson, 1995), chapter 102 for a description of techniques used in CADD. Also included within the scope of the invention are mimetics prepared using such techniques that produce either peptides or conventional organic pharmaceuticals that specifically inhibit binding of MPO to the MPO binding site of apo A1 as determined using a competitive binding assay Generally, peptidomimetics are structurally similar to a paradigm polypeptide (i.e., SEQ. ID NO: 2 described herein), but have one or more peptide linkages optionally replaced by a linkage selected from the group consisting of: —$CH_2NH$—, —$CH_2S$—, —$CH_2CH_2$—, —CH.dbd.CH— (cis and trans), —$COCH_2$—, —$CH(OH)CH_2$—, —$CH_2SO$—, etc. by methods known in the art and further described in the following references: Spatola (1983) p. 267 in Chemistry and Biochemistry of Amino Acids, Peptides, and Proteins, B. Weinstein, eds., Marcel Dekker, New York; Spatola (1983) Vega Data 1(3) Peptide Backbone Modifications. (general review); Morley (1980) Trends Pharm Sci pp. 463-468 (general review); Hudson et al. (1979) Int J Pept Prot Res 14:177-185 (—$CH_2NH$—, $CH_2CH_2$—); Spatola et al. (1986) Life Sci 38:1243-1249 (—$CH_2$—S); Hann, (1982) J Chem Soc Perkin Trans 1307-314 (—CH—CH—, cis and trans); Almquist et al. (1980) J Med Chem. 23:1392-1398 (—CO $CH_2$—); Jennings-White et al. (1982) Tetrahedron Lett. 23:2533 (—CO $CH_2$—); Szelke, M. et al., European Appln. EP 45665 (1982) CA: 97:39405 (1982) (—CH(OH) $CH_2$—); Holladay et al. (1983) Tetrahedron Lett 24:4401-4404 (—C(OH)$CH_2$—); and Hruby (1982) Life Sci., 31:189-199 (—$CH_2$—S—)). Such peptide mimetics may have significant advantages over polypeptide embodiments, including, for example: more economical production, greater chemical stability, enhanced pharmacological properties (half-life, absorption, potency, efficacy, etc.), reduced antigenicity, and others. By employing, e.g., scanning mutagenesis, e.g., alanine scanning mutagenesis, linker scanning mutagenesis or saturation mutagenesis, to map the amino acid residues of a particular LBP polypeptide involved in binding a binding molecule, peptide mimetics, e.g., diazepine or isoquinoline derivatives, can be generated The organo-mimetic has a molecular weight under 10 kDa, preferably with a molecular weight of 2 kDA or less and appropriate structural similarity to a peptide that inhibits binding of MPO to the MPO-binding site of Apo A-1 may be also used as the AMBI. As one of skill in the art understands, small molecule mimetics are chemically synthesized compounds that provide the spatial conformation necessary to properly associate to a particular protein and elicit a response. Therefore, the present invention also comprises the use of a small molecule mimetic to inhibit binding of MPO to the MPO binding site.

Methods of Preparing the Peptide

The apoA1 peptides of the present invention are prepared using standard techniques and equipment for preparing synthetic peptides, such as a synthesizer. For example, the apoA1 peptide may be prepared using the 9600 Millegen/Biosearch synthesizer or a 40 well multiple peptide synthesizer (MPS 396, Advanced Chem Tech, Lousiville, Ky.) and purified by reverse phase HPLC (Water's Associates) and characterized by electrospray ionization spectrometry. Retro-inverso peptides are assembled in a reverse order of amino acids with Fmoc-D-aminoacid derivatives.

D-amino acids are incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form amino acids can be incorporated at any position in the peptide as desired. Thus, for example, in one embodiment, the peptide can comprise a single D-amino acid, while in other embodiments, the peptide comprises at least two, three, four, five, six, seven, eight, nine, ten, eleven, twelve, thirteen, fourteen, or in some embodiments, even more D amino acids.

Protecting/blocking groups are well known to those of skill as are methods of coupling such groups to the appropriate residue(s) comprising the peptides of this invention (see, e.g., Greene et al., (1991) *Protective Groups in Organic Synthesis,* 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

In addition, circular permutations of the peptides described herein or constrained peptides (including cyclized peptides) comprising a consensus sequence or a substantially identical consensus sequence variation may be generated by methods known in the art (Rizo and Gierasch (1992) Ann. Rev. Biochem. 61: 387); for example, by adding internal cysteine residues capable of forming intramolecular disulfide bridges which cyclize the peptide.

Methods for Treating Subjects Having or at Risk of Having or Developing CVD

The present invention provides methods comprising administering one or more of the present AMBI to a subject in need of the same. Thus, the present methods are useful for treating subjects who have a cardiovascular disease, e.g. coronary disease. Such subjects have been diagnosed as having a cardiovascular disease or have exhibited a complication of a cardiovascular disease. Medical procedures for determining whether a human subject has coronary artery disease or is at risk for experiencing a complication of coronary artery disease include, but are not limited to, coronary angiography, coronary intravascular ultrasound (IVUS), stress testing (with and without imaging), assessment of carotid intimal medial thickening, carotid ultrasound studies with or without implementation of techniques of virtual histology, coronary artery electron beam computer tomography (EBTC), cardiac computerized tomography (CT) scan, CT angiography, cardiac magnetic resonance imaging (MRI), and magnetic resonance angiography (MRA.). The present methods are also useful for treating subjects at risk of having a cardiovascular disease, i.e., subjects who are positive for at least one risk factor, e.g. elevated levels of circulating MPO, hypertension, family history of premature CVD, smoking, high total cholesterol, low HDL cholesterol, obesity, diabetes, etc. Because cardiovascular disease, typically, is not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease. Subjects who are at risk of having cardiovascular disease are at risk of having an abnormal stress test or abnormal cardiac catherization. Subjects who are at risk of having CVD are also at risk of exhibiting increased carotid intimal medial thickness and coronary calcification, characteristics that can be assessed using non-invasive imaging techniques. Subjects who are at risk of having CVD are also at risk of having an increased atheroscleorotic plaque burden, a characteristic that can be examined using intravascular ultrasound. The present invention is also useful for treating adults who are apparently healthy, i.e., who have none of the risk factors for cardiovascular disease, and who are non-smokers. Veterinary uses are also contemplated. Thus, while the present methods are particularly useful for treating human subjects, they may also be used to treat other mammals.

Typically, one or a combination of AMBI are administered to the subject in the form of a pharmaceutical composition. The present invention also provides methods that comprise administering one or more AMBI to the subject in combination with another therapeutic agent for cardiovascular disease. Examples of such agents include, but are not limited to an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, and/or combinations thereof.

Pharmaceutical Composition

The pharmaceutical composition comprises an efficacious amount of the present peptide, peptide mimetic, or small organic molecule and preferably a relatively inert topical carrier. Many such carriers are routinely used and can be identified by reference to pharmaceutical texts.

The acceptable carrier is a physiologically acceptable diluent or adjuvant. The term physiologically acceptable means a non-toxic material that does not interfere with the effectiveness of the antagonist. The characteristics of the carrier will depend on the route of administration and particular compound or combination of compounds in the composition. Preparation of such formulations is within the level of skill in the art. The composition may further contain other agents which either enhance the activity of present peptide, peptide mimetic, or small organic molecule, or complement its activity. The composition may further comprise fillers, salts, buffers, stabilizers, solubilizers, and other materials well known in the art.

Dosage

In vivo, an effecacious amount is an amount sufficient to show a meaningful benefit, i.e., sufficient to treat, heal, prevent or slow the development of cardiovascular disease or to partially or completely relieve the symptoms associated with cardiovascular disease, or to lower the levels of a diagnostic marker for such disease. The amount of the AMBI required will depend upon the nature and severity of the condition being treated, and on the nature of prior treatments which the subject has undergone. Ultimately, the dosage will be determined using clinical trials. Initially, the clinician will administer doses that have been derived from animal studies. An effective amount can be achieved by one administration of the composition. Alternatively, an effective amount is achieved by multiple administration of the composition to the subject. The efficacy of oral, subcutaneous and intravenous administration is determined in clinical studies.

The AMBI may be administered by any suitable route that ensures bioavailability in the circulation. This can best be achieved by parenteral routes of administration, including intravenous (IV), intramuscular (IM), intradermal, subcutaneous (SC) and intraperitoneal (IP) injections. However, other routes of administration may be used. For example, absorption through the gastrointestinal tract can be accomplished by oral routes of administration (including but not limited to ingestion, buccal and sublingual routes) provided appropriate formulations (e.g., enteric coatings) are used to avoid or minimize degradation of the active ingredient, e.g., in the harsh environments of the oral mucosa, stomach and/or small intestine. Alternatively, administration via mucosal tissue such as vaginal and rectal modes of administration may be utilized to avoid or minimize degradation in the gastrointestinal tract. In yet another alternative, the formulations of the invention can be administered transcutaneously (e.g., transdermally), or by inhalation. It will be appreciated that the preferred route may vary with the condition, age and compliance of the recipient.

The actual dose of AMBI used will vary with the route of administration, and should be adjusted to achieve circulating plasma concentrations of an amount sufficient to show a meaningful clinical benefit without toxicity, something ultimately determined empirically in clinical studies. Toxicity and therapeutic efficacy of the various AMBI can be determined using standard pharmaceutical procedures in cell culture or experimental animals for determining the LD.sub.50 (the dose lethal to 50% of the population) and the ED.sub.50 (the dose therapeutically effective in 50% of the population). The dose ratio between toxic and therapeutic effects is the therapeutic index and it can be expressed as the ratio $LD_{50}/ED_{50}$. AMBI. AMBI that exhibit large therapeutic indices are preferred.

The agent is administered in an amount effective to lower the risk of the subject developing a future cardiovascular disorder.

It is further contemplated that, while peptides and polypeptides may be employed in methods of the invention, they may be first provided as a nucleic acid that is transcribed and translated into the desired proteinaceous compound. The nucleic acid may be an expression construct. In some embodiments an expression construct is a viral vector, such as an adenovirus, adeno-associated virus, herpesvirus, lentivirus, retrovirus, vaccinia virus, or other viruses vectors employed with respect to gene transfer.

Method of Identifying or Screening For Compounds for Treating Cardiovascular Disease.

The present invention also provides methods for identifying or screening compounds that have the potential to treat cardiovascular disease or attenuate the progression of atherosclerotic plaque. Such compounds include peptides, peptide mimetics or small organic molecules having a molecular weight of less than 10 kDa, or a product of natural, semi-synthetic, or synthetic combinatorial library. The method comprises identifying or screening for compounds that block, inhibit or reduce binding of MPO with HDL. In one embodiment, the method comprises incubating the compound, referred to hereinafter as a "test compound", with a molecule that comprises the MPO binding site of apoA-1 under conditions that allow MPO to bind to the MPO binding site. Typically, the test compound, MPO and the molecule will be incubated in a physiologic solution or buffer. Then, the binding of MPO with the molecule is assessed. The test agent, MPO, and the molecule may be added to the incubation medium concurrently or sequentially, in any order. Thus, the test agent may first be incubated with MPO and then the molecule comprising the MPO binding site of apoA1 may be added to the incubation medium. Alternatively, MPO and the molecule comprising the MPO binding site of apoA1 may be added to the incubation medium prior to addition of the test compound. Alternatively, the test compound and the molecule comprising the MPO binding site of apoA1 may be added to the incubation medium before MPO is added to the incubation medium.

In certain embodiments, the methods comprise a control study in which binding of MPO to the molecule is assessed in the absence of the test compound, and then compared to the level of binding that occurs in the test study, i.e., when MPO or a molecule comprising the MPO binding site of apo A1 is contacted with the test compound. Such control study allows one to determine the degree to which the test compound inhibits binding of MPO to the MPO binding site of apo A1. Although desirable, the control study need not be run in parallel with the test study, and may consist of experimentation done days, weeks, or months in advance of the test study. A decrease in binding of MPO to a fragment of apo A-1 comprising the MPO binding site of apo A-1, apo A-1, or HDL in the presence of the test compound relative to the binding that occurs in the absence of the test compound indicates that the test compound has the potential to prevent or treat cardiovascular disease in a subject, particularly a human subject. In certain embodiments, the inhibitory activity of the test molecule is compared to the inhibitory activity of a peptide comprising SEQ ID NO: 2 or SEQ ID NO:3.

The binding of MPO to the molecule comprising the MPO binding site of apoA-1 may be assessed by techniques well known in the art, and need not be discussed in detail here. Exemplary techniques for assessing the effect of the test compound on binding of binding of MPO to the MPO binding site of apo A1 may also include attaching the target molecule, e.g. MPO, or the molecule comprising the MPO binding site of apo A1, or both to a substrate. Attachment of the target molecule facilitates washing and removal of unreacted target molecule and test compound from the assay. In certain embodiments, the assay involves immobilizing HDL, apo A1 or an apo A1 fragment comprising the MPO binding site to a solid support, and then assessing the impact of putative AMBI on MPO binding by co-incubation with the immobilized HDL, apo A1 or the apo A1 fragment on the solid support, washing, and then quantifying MPO bound to the solid support. This can be achieved by any of many methods of quantifying MPO including by its direct catalytic activity (e.g. with $H_2O_2$ and a peroxidase chromaphore), or MPO mass (e.g. like a sandwich ELISA using a anti-MPO Ab and subsequent visualization method). Exemplary techniques for assessing the effect of the test compound on binding of MPO to the MPO binding site of apo A1, may also include for example, labeling the molecule, referred to hereinafter as the "target molecule", that is contacted with the test compound with a label such as a radioactive isotope or fluorescent labels. Examples of such labels include, but are not limited to biotin, fluorescein, Texas red, Lucifer yellow, and rhodamine. Other labeling methods include electron dense tracers, such as alkaline phosphatase, horeseradish peroxidase, and glucose oxidase.

Experimental conditions for the present method include, for example, pH, temperature, duration of contact between the test compound and the target molecule, concentration of test compound in the contact solution, number and duration of washes that occur after the test compound is contacted with the target molecule or after the reacted test compound and target molecule are exposed to the binding partner of the target molecule, composition of the wash solutions, and the like. Preferred experimental conditions include, for example, pH of 7.0, temperature of from 0-37° C., contact of the test compound with the target molecule of from 0.1 second to 10 hours. The present methods may be run in physiologic buffers or serum. Wash solutions my be any aqueous vehicle including, but not limited to water, saline Ringer, HEPES buffer, or Tris buffer plus or minus detergents and added salts. In certain instances, the screening method comprises contacting the target molecule with different concentrations of the test compound.

A test agent can be any type of molecule, including, for example, a peptide, a peptidomimetic, a peptoid such as vinylogous peptoid, a polynucleotide, or a small organic molecule, that one wishes to examine for the ability to inhibit binding of MPO to the MPO binding site of apo A-1. It will be recognized that a method of the invention is readily adaptable to a high throughput format and, therefore, the method is convenient for screening a plurality of test agents either serially or in parallel. A such, a test agent can be one of a plurality of test agents, for example, a library of test agents produced by a combinatorial method. Methods for preparing a combinatorial library of molecules that can be tested for inhibition of MPO-Apo A-1 are well known in the art and include, for example, methods of making a phage display library of peptides, which can be constrained peptides (see, for example, U.S. Pat. No. 5,622,699; U.S. Pat. No. 5,206,347; Scott and Smith, Science 249:386-390, 1992; Markland et al., Gene 109:13-19, 1991; each of which is incorporated herein by reference); a peptide library (U.S. Pat. No. 5,264,563, which is incorporated herein by reference); a peptidomimetic library (Blondelle et al., Trends Anal. Chem. 14:83-92, 1995; a nucleic acid library (O'Connell et al., supra, 1996; Tuerk and Gold, supra, 1990; Gold et al., supra, 1995; each of which is incorporated herein by reference); an oligosaccharide library (York et al., Carb. Res., 285:99-128, 1996; Liang et al., Science, 274:1520-1522, 1996; Ding et al., Adv. Expt. Med. Biol., 376:261-269, 1995; each of which is incorporated herein by reference); a lipoprotein library (de Kruif et al., FEBS Lett., 399:232-236, 1996, which is incorporated herein by reference); a glycoprotein or glycolipid library (Karaoglu et al., J. Cell Biol., 130:567-577, 1995, which is incorporated herein by reference); or a chemical library containing, for example, drugs or other pharmaceutical agents (Gordon et al., J. Med. Chem., 37:1385-1401, 1994; Ecker and Crooke, BioTechnology, 13:351-360, 1995; each of which is incorporated herein by reference).

The capacity of the test agent to inhibit binding of MPO to, HDL, apo A-1, or the MPO binding site of apo A1, can be reported as an affinity constant (Kd or Ka), or the concentration of test agent required for 50% inhibition (IC.sub.50 values) of specific binding of MPO. Specific binding is preferably defined as the total binding (e.g., total label in complex) minus the non-specific binding. Non-specific binding is preferably defined as the amount of label detected in binding complexes formed in the presence of excess unlabeled MPO.

EXAMPLES

The following examples are included for purposes of illustration and are not intended to limit the scope of the invention.

Example 1

Identifying the MPO Binding Site on Apolipoprotein A-1

Substantial evidence supports the notion that oxidative processes participate in the pathogenesis of atherosclerotic heart disease (Chisolm, G. M., et al., Free Radical Biology & Medicine. 28:1815-1826, Lusis, A. J. 2000, Nature. 407:233-241, Navab, M., et al., 2002, Current Opinion in Lipidology. 13:363-372, Podrez, E. A., et al., 2000, Free Radical Biology & Medicine. 28:1717-1725, Heinecke, J. W. 2003, American Journal of Cardiology. 91:12A-16A.). One such oxidative pathway that appears to be involved is formation of nitric oxide-(NO, nitrogen monoxide) derived oxidants (Beckman, J. S., et al., 1996, American Journal of Physiology. 271:C1424-1437, Beckman, J. S., et al., 1994, Methods in Enzymology 233:229-240, Leeuwenburgh, C., et al., 1997, Journal of Biological Chemistry. 272:1433-1436, Podrez, E. A., et al., 1999, Journal of Clinical Investigation. 103:1547-1560, Shishehbor, M. H., et al., 2003, JAMA. 289:1675-1680.). NO typically functions as a potent vasodilator and inhibitor of platelet aggregation, leukocyte adhesion, and smooth muscle cell proliferation (Kinlay, S., et al., 2001, Current Opinion in Lipidology. 12:383-389, Moncada, S. 1999, Journal of the Royal Society of Medicine. 92:164-169, Ignarro, L. J., et al., 2002, Circulation Research. 90:21-28.). However, under pathological conditions such as during inflammation and cardiovascular disease (CVD), NO may be converted into potent nitrating oxidants that promote oxidative damage, cell injury and conversion of low-density lipoprotein (LDL), the major carrier of cholesterol in plasma, into an atherogenic form (Podrez, E. A., et al., 1999, Journal of Clinical Investigation. 103:1547-1560, Graham, A., et al., 1993, FEBS Letters. 330:181-185). Protein bound nitrotyrosine ($NO_2Tyr$), a post-translational modification specific for protein oxidation by NO-derived oxidants (MacMillan-Crow, L. A., et al., 1996, Proceedings of the National Academy of Sciences of the United States of America. 93:11853-11858, Hazen, S. L., et al., 1999, Methods in Enzymology 300:88-105, Brennan, M. L., et al., 2002, Journal of Biological Chemistry. 277:17415-17427, van der Vliet, A., et al., 1997, Journal of Biological Chemistry. 272:7617-7625, Eiserich, J. P., et al., 1998, Nature. 391:393-397, Wu, W., et al., 1999, Journal of Biological Chemistry. 274:25933-25944.), is markedly enriched within human atheroma (Leeuwenburgh, C., et al., 1997, Journal of Biological Chemistry. 272:1433-1436, Beckmann, J. S., et al., 1994, Biological Chemistry Hoppe-Seyler. 375:81-88). Further, recent clinical studies demonstrate that systemic levels of protein-bound $NO_2Tyr$ serve as an independent predictor of atherosclerotic risk and burden in subjects and are modulated by known CVD risk-reducing therapies such as statins (Shishehbor, M. H., et al., 2003, JAMA. 289:1675-1680, Shishehbor, M. H., et al., 2003, Circulation. 108:426-431). Few studies to date have focused upon defining the molecular targets of nitration in subjects with CVD, the attendant functional alterations, and the enzymatic participants in nitration.

One potential enzymatic source for generation of NO-derived oxidants within human atheroma is the heme protein myeloperoxidase (MPO). MPO utilizes hydrogen peroxide ($H_2O_2$) and a variety of low molecular weight organic and inorganic substances as substrates to form reactive oxidant species capable of promoting protein halogenation, nitration and oxidative cross-linking (Podrez, E. A., et al., 2000, *Free Radical Biology & Medicine*. 28:1717-1725, Heinecke, J. W. 2003, *American Journal of Cardiology*. 91:12A-16A). For example, MPO directly utilizes both NO (Abu-Soud, H. M., et al., 2000, *Journal of Biological Chemistry*. 275:37524-37532) and the NO metabolite nitrite ($NO_2^-$) as substrates in vitro (Brennan, M. L., et al., 2002, *Journal of Biological Chemistry*. 277:17415-17427, van der Vliet, A., et al., 1997, *Journal of Biological Chemistry*. 272:7617-7625, Eiserich, J. P., et al., 1998, *Nature*. 391:393-397, Burner, U., et al., 2000, *Journal of Biological Chemistry*. 275:20597-20601), and participates in both protein nitration and initiation of lipid peroxidation in vivo (Brennan, M. L., et al., 2002, *Journal of Biological Chemistry*. 277:17415-17427, Zhang, R., et al., 2002, *Journal of Biological Chemistry*. 277:46116-46122, Baldus, S., et al., 2001, *Journal of Clinical Investigation*. 108:1759-1770, Gaut, J. P., et al., 2002, *Journal of Clinical Investigation*. 109:1311-1319). MPO (Daugherty, A., et al., 1994, *Journal of Clinical Investigation*. 94:437-444, Sugiyama, S., et al., 2001, *American Journal of Pathology*. 158:879-891), and multiple specific oxidation products formed by the enzyme (Leeuwenburgh, C., et al., 1997, *Journal of Biological Chemistry*. 272:1433-1436, Hazen, S. L., et al., 1999, *Methods in Enzymology* 300:88-105, Hazen, S. L., et al., 2000, *Biochemical Journal* 3:693-699, Thukkani A. K., et al., 2003, *Circulation* 108:3128-3133), are markedly enriched within human atherosclerotic lesions. Further, recent clinical studies demonstrate that elevated levels of MPO both are seen in patients with angiographic evidence of cardiovascular disease (CVD) (Zhang, R., et al., 2001, *JAMA*. 286:2136-2142) and predict incident risks for myocardial infarction, revascularization, and cardiac death in subjects presenting with chest pain or acute coronary syndrome (Brennan, M. L., et al., 2003, *New England Journal of Medicine*. 349:1595-1604, Baldus, S., et al., 2003, *Circulation*. 108:1440-1445). Accordingly, defining targets of oxidative modification by MPO- and NO-generated oxidants, and potential functional consequences that result, is of considerable interest.

In the present study we have begun the process of identifying protein targets that are nitrated in serum of subjects with CVD. Early preliminary studies identified enrichment in nitrotyrosine content within apolipoprotein A-I (apoA-I), the major protein constituent within high density lipoprotein (HDL). Further analyses reveal that MPO binds to apoA-I and likely serves as the major enzymatic catalyst for apoA-I nitration in vivo, selectively targeting the lipoprotein for MPO-catalyzed nitration and halogenation within human atheroma. In vitro studies demonstrate that MPO-catalyzed oxidative modification of HDL or apoA-I is accompanied by selective impairment in ABCA1-dependent cholesterol efflux function of the lipoprotein. In vivo evidence for a functional role of MPO- and NO-derived oxidants in the inhibition of apoA-I cholesterol efflux activity in subjects was obtained by observing a significant correlation between higher apoA-I nitrotyrosine and chlorotyrosine content of isolated HDL and diminished ABCA1-dependent cholesterol efflux activity of the lipoprotein. The present studies suggest that MPO—apoA-I interactions may play an important role in development of "dysfunctional" or "pro-inflammatory" HDL and the atherosclerotic phenotype.

Materials and Methods

Materials

L-[$^{13}C_6$]tyrosine and L-[$^{13}C_9$, $^{15}N_1$]tyrosine were purchased from Cambridge Isotopes Inc. (Andover, Mass.). Tissue culture media and additives were purchased from Life Technologies (Gaitherburg, Md.). RAW264.7 cells were obtained from the American Type Culture Collection (Rockville, Md.). [$^3$H]Cholesterol was obtained from Amersham (Piscataway, N.J.), and resuspended in ethanol prior to use. All other reagents were obtained from Sigma Chemical Co. (St. Louis, Mo.) unless otherwise specified.

Methods

General procedures. Peroxynitrite was synthesized and quantified as described (Beckman, J. S., et al., 1994, *Methods in Enzymology* 233:229-240). L-3-[$^{13}C_6$]nitrotyrosine was synthesized from L-[$^{13}C_6$]tyrosine and peroxynitrite, and isolated by reverse phase HPLC to remove residual $NO_2^-$ prior to use (Wu, W., et al., 1999, *Journal of Biological Chemistry*. 274:25933-25944). Protein content was determined by the Markwell-modified Lowry protein assay (Markwell, M. A., et al., 1978, *Analytical Biochemistry*. 87:206-210) with bovine serum albumin as standard. The concentration of reagent $H_2O_2$ was determined spectrophotometrically ($\epsilon_{240}$=39.4 $M^{-1}$ $cm^{-1}$; ref. (Nelson, D. P., et al., 1972, *Analytical Biochemistry*. 49:474-478). Myeloperoxidase (donor: hydrogen peroxide, oxidoreductase, EC 1.11.1.7) was initially purified from detergent extracts of human leukocytes by sequential lectin affinity and gel filtration chromatography as described by Rakita (Rakita, R. M., et al., 1990, *Biochemistry*. 29:1075-1080), and then trace levels of contaminating eosinophil peroxidase were then removed by passage over a sulphopropyl Sephadex column (Wever, R., et al., 1981, *FEBS Letters*. 123:327-331). Purity of isolated MPO was established by demonstrating a RZ of >0.84 ($A_{430}/A_{280}$), SDS PAGE analysis with Coomassie Blue staining, and in-gel tetramethylbenzidine peroxidase staining (van Dalen, C. J., et al., 1997, *Biochemical Journal*. 327:487-492). Enzyme concentration was determined spectrophotometrically utilizing an extinction coefficient of 89,000 $M^{-1}$ $cm^{-1}$/heme of MPO (Agner, K., 1972. *Structure and function of oxidation-reduction enzymes*. Tarrytown, N.Y.: Pergamon Press. 329-335). Delipidated and purified apoA-I was purchased from Biodesign International (Saco, Me.) and used without further purification following demonstration of purity by SDS-PAGE and silver stain analysis, and lack of significant free fatty acids by HPLC with on-line tandem mass spectrometry analysis (Zhang, R., et al., 2002, *Journal of Biological Chemistry*. 277:46116-46122). Low density lipoprotein (LDL; 1.019<d<1.063 g/ml fraction) and high density lipoprotein (HDL; 1.063<d<1.21 g/ml fraction) were isolated from fresh plasma by sequential ultracentrifugation (Hatch, F. T., 1968, *Advances in Lipid Research* 6:1-68). Final preparations were extensively dialyzed against 50 mM sodium phosphate (pH 7.0), 200 µM diethylenetriaminepentaacetic acid (DTPA) and stored under $N_2$ until use. LDL was acetylated with acetic acid anhydride (Goldstein, J. L., et al., 1979, *Proceedings of the National Academy of Sciences of the United States of America*. 76:333-337). $NO_2$Tyr immunostaining was performed as described (MacPherson, J. C., et al., 2001, *Journal of Immunology*. 166:5763-5772). Specificity of immunostaining for $NO_2$Tyr was confirmed by showing loss of staining (i) in competition studies with 10 mM nitrotyrosine present during antibody-antigen incubations; and (ii) upon reduction of sample with dithionite.

Clinical specimens—Serum. For studies involving mass spectrometry-dependent quantification of serum total protein, apoA-I and apoB-100 contents of $NO_2Tyr$ and $ClTyr$, sequential patients (n=45) with cardiovascular disease (CVD) receiving care from the Preventive Cardiology Clinic of the Cleveland Clinic Foundation and healthy volunteers (n=45) responding to advertisements were enrolled. CVD was defined clinically as coronary artery disease, peripheral arterial disease, or cerebral vascular disease. Subjects with CVD were stable and without cardiac symptoms. Patients who experienced a myocardial infarction or stroke within one month preceding enrolment were ineligible. Studies correlating HDL levels of $NO_2Tyr$ and $ClTyr$ with ABCA1-dependent cholesterol efflux activities were performed on a separate sequential set of subjects (n=12) without known (CVD) receiving care from the Preventive Cardiology Clinic. All participants gave written informed consent and the Institutional Review Board of the Cleveland Clinic Foundation approved the study protocol. Clinical investigations were conducted in accordance with the Declaration of Helsinki principles. A medical history and record review was performed to define coronary risk factors, including diabetes mellitus (defined by fasting blood glucose >125 mg/dl or hypoglycemic medications), hypertension (blood pressure >140/90 or anti-hypertensive medications in the absence of known cardiac disease), family history of premature coronary heart disease (first degree relative with coronary heart disease prior to age 60 by subject report), history of hypercholesterolemia (fasting LDL cholesterol >160 mg/dl or lipid lowering medications in the absence of known cardiac disease), and cigarette smoking (any smoking within 1 year of study). A fasting blood sample was obtained using a serum separator tube. Serum was isolated, aliquots placed into cryovials supplemented with antioxidant cocktail comprised of butylated hydroxytoluene (100 μM final) and DTPA (2 mM final, pH 7.0), covered in argon and snap frozen at −80° C. until time of analysis.

*Immuno-affinity purification of nitrated proteins.* An ImmunoPure Protein A Orientation Kit (Pierce) was utilized to affinity-purify nitrated proteins from albumin/IgG depleted serum. Briefly, human serum (45 μl) was depleted of albumin and IgG using the ProteoPrep Albumin Depletion Kit (Sigma-Aldrich Corp., St. Louis, Mo.) as recommended by the manufacturer. Affinity purified anti-nitrotyrosine antibody raised against a synthetic octapeptide (Cys-Gly-$NO_2$Tyr-Gly-Gly-Gly-$NO_2$Tyr-Gly; SEQ ID NO: 5) was bound to protein A and cross-linked with dimethylpimelimidate. The albumin/IgG depleted patient serum was diluted in 0.15 M NaCl, 0.1 M phosphate, pH 7.2, and applied to the column. Unbound protein fractions were eluted with 20 ml of PBS, and 10 ml of 0.5 M NaCl. The bound proteins were eluted with 5 mM 3-nitrotyrosine in 0.5 M NaCl. The bound fractions were concentrated using Centriprep filter devices (YM-10, Millipore), dialyzed against 0.1 M urea, and dried down to a small volume using a Savant Instrument Speed-Vac Concentrator (Savant Instruments Inc., Holbrook, N.Y.) Protein in the fractions was monitored with the bicinchoninic acid assay (Pierce), using BSA as standard.

2D SDS-PAGE. After dialysis, approximately 50 μg of protein was added to 155 μl sample rehydration buffer and absorbed overnight onto 7 cm pH 3-10 non-linear IPG ZOOM strips (Invitrogen). Isoelectric focusing was carried out using the ZOOM IPG runner system from Invitrogen and the Biorad 3000V power supply using the following voltage step protocol: 100 V for 30 min, 200 V for 20 min, 450 V for 15 min, 750 V for 15 min, and 2000 V for 30 min. For the second dimension, focused IPG strips were equilibrated in LDS sample buffer (Invitrogen) in the presence of NUPAGE sample reducing agent (Invitrogen) for 15 min, and an additional incubation in LDS sample buffer in the presence of 125 mM iodoacetamide for 15 min. The strips were placed on 4-12% bis-tris gels and embedded in 0.5% agarose (w/v). The gels were stained for protein using either colloidal blue or silver staining. For immunoblotting gels were transferred to 0.2 □m Immun-Blot PVDF membranes (Bio-Rad, Hercules, Calif.).

Clinical specimens—Tissue. LDL-like and HDL-like particles were isolated from atherosclerotic lesions from aortas and femoral artery tissues obtained at autopsy (tissue harvest within 10 h of death). Control studies to confirm that post mortem artifacts were not significant utilized vascular tissues (n=5) obtained fresh at the time of vascular surgery. Normal human aortic tissues were obtained from transplant donors. All tissues were immediately rinsed in ice-cold phosphate buffered saline supplemented with 100 μM DTPA and immediately frozen in Buffer A (65 mM sodium phosphate, pH 7.4, 100 μM DTPA, 100 μM butylated hydroxy toluene), under $N_2$ at −80° C. until analysis.

LDL- and HDL-like particle isolation and characterization from normal human aortic tissues and human atherosclerotic lesions. LDL- and HDL-like particles were isolated from fatty streaks and intermediate lesions of human thoracic aortae by sequential density ultracentrifugation (d=1.019-1.070 g/ml fraction for "lesion LDL", 1.063-1.21 g/ml fraction for "lesion HDL") using a modification of the method of Steinbrecher and Lougheed (Steinbrecher, U. P., et al., 1992, *Arteriosclerosis & Thrombosis*. 12:608-625) as described (Krul, E. S., et al., 1992, *Biochemical & Biophysical Research Communications*. 189:1069-1076). "Control Aortic LDL" and "Control Aortic HDL"-like particles were similarly isolated from residual aortic tissues free of visible atherosclerotic plaque from transplant donors. A metal chelator (100 μM DTPA), myeloperoxidase inhibitor (10 mM 3-aminotriazole), and protease cocktail comprised of PMSF and Sigma protease inhibitor cocktail (catalog No P8340) were included in all solutions used for lipoprotein isolation. Control Aortic and Lesion LDL and HDL were subjected to SDS-PAGE (Laemmli, U. K., 1970, *Nature*. 227:680-685) with Western blot analysis using either a rabbit anti-human apoB-100 antiserum (Hazen, S. L., et al., 1997, *Journal of Clinical Investigation*. 99:2075-2081), or goat anti-human apoA-I (Biodesign, Saco, Me.), respectively. Analysis of Control Aortic and Lesion LDL-like particles with polyclonal antibody to apoB-100 detected a 500 kDa protein, the mass of intact apolipoprotein B100. As previously noted (Krul, E. S., et al., 1992, *Biochemical & Biophysical Research Communications*. 189:1069-1076), both aggregated/cross-linked and lower molecular mass forms of immunoreactive protein were also present in LDL-like particles isolated from vascular tissues. Similar Western analyses were performed on Control Aortic and Lesion HDL-like particles using antibodies to apoA-I, confirming the presence of apoA-I. Analysis of Control Aortic and Lesion LDL-like particles by high resolution size exclusion chromatography (tandem Superose 6 and 12 columns; Pharmacia LKB) demonstrated that immunoreactive apoB-100, total cholesterol, and the majority of protein mass exhibited an apparent $M_r$ similar to that of LDL isolated from plasma. Identity of apoA-I as a major protein constituent present in Control Aortic and Lesion HDL-like particle preparations was also achieved by tandem MS sequence analysis following excision from Coomassie blue stained SDS PAGE gels.

Several control experiments indicated that post-mortem changes were unlikely to contribute to apoA-I nitration and chlorination. First, control studies were performed on fresh arterial tissues harvested at time of vascular surgery (for lesion) and organ harvest for transplantation (for normal/non-lesion arterial tissues). Comparable levels of $NO_2Tyr$ and ClTyr were noted within these freshly harvested vascular tissues, compared to those obtained at autopsy. Second, following generation of powdered aortic tissues using a stainless steel mortar and pestle at liquid nitrogen temperatures, incubation of aortic tissue powder (suspended in PBS) with MPO (100 nM) for 10 h at room temperature failed to increase levels of $NO_2Tyr$ or ClTyr, as monitored by both mass spectrometry and SDS-PAGE and Western analyses (for $NO_2Tyr$). Third, control studies demonstrated no significant formation of 3-[$^{13}C_6$]ClTyr or 3-[$^{13}C_6$]$NO_2Tyr$ in the above aortic tissue powder/MPO mixtures supplemented with L-[$^{13}C_6$]tyrosine, incubated at room temperature for 10 h, and then subjected to mass spectrometry analysis.

Co-immunoprecipitation study. Human MPO (67 □g) was added to 450 □l of human plasma from a normal healthy donor. Aliquots (75 □l each) were used for immunoprecipitation studies with the indicated IgG by first mixing with 20 □l of either goat anti human apoA-I (Biodesign), rat anti human MPO (Dako), or non-immune mouse IgG as a control. Individual mixtures were then diluted with 0.4 ml PBS and incubated with 80 □l of Protein G sepharose slurry/beads (Pierce). The antibody-antigen complexes were pelleted by centrifugation, and the supernatant was removed and saved. After washing, immune complexes in the pellets were recovered from the Protein G sepharose beads.

Hydrogen/deuterium exchange mass spectrometry. Separate aliquots of HDL (85 µg protein) and human MPO (21 µg) were deuterium-labeled by mixing with 50 µl of $D_2O$ containing 50 mM $ND_4OAc$, pD 7.0 at room temperature for 1 h. The deuterated HDL was combined with either deuterated MPO or additional deuterium buffer and incubated for 1 h at room temperature to allow binding. The combined HDL/MPO and the apoA-I alone samples were concentrated to 10 µl by centrifugation through a 10 kDa molecular weight cut-off filter. The retentate was subsequently diluted to 200 µL with 50 mM $NH_4OAc$, pH 7.0 for 10 minutes for back (off)-exchange before quenching by rapidly cooling on ice/methanol bath and adding 10 µL 10% TFA to reduce the pH. Proteins were digested with immobilized pepsin that had been pre-washed with ice-cold 0.1% TFA. The pepsin digestion was carried out for 5 min, immediately filtered to remove the residual pepsin beads, and then samples were immediately injected for analysis by HPLC-MS/MS. A 1 mm×3 cm C18 reversed phase column (Grace Vydac, Hesperia, Calif.) was used to fractionate peptides. The injector, analytical column and tubings were all maintained at 0° C. by immersion in ice/water bath during analysis to minimize back exchange. An aliquot of the sample was injected using a pre-chilled syringe. Peptides were eluted with a linear gradient of 2%-80% acetonitrile in 0.05% TFA over 10 min. An LCQ Deca ion trap mass spectrometer (ThermoFinnigan, San Jose, Calif.) was used to record full scan spectra containing well-resolved isotopic peaks for the respective peptides, as well as collision-induced dissociation (CID) spectra.

HDL and apoA-I nitration and chlorination in vitro. HDL and apoA-I modifications were carried out in 50 mM phosphate buffer, pH 7.0, containing 100 µM DTPA, 1 mg/mL HDL protein, 57 µM MPO, and either 100 µM nitrite (for the nitration reactions) or 100 mM chloride (for the chlorination reactions). Hydrogen peroxide (100 µM final) was added to initiate reactions. Peroxynitrite (100 µM) was added as a rapid single bolus addition where specified.

Cholesterol efflux studies. Cholesterol efflux experiments were performed according to established procedures (Kinter, M., et al., 2000, *Protein Sequencing and Identification Using Tandem Mass Spectrometry*, Willard, B. B., et al., 2003, *Analytical Chemistry*. 75:2370-2376). Briefly, subconfluent RAW264 cells in 24-well dishes were cholesterol-loaded and labeled overnight in 0.5 ml of DGGB (DMEM supplemented with 50 mM glucose, 2 mM glutamine, and 0.2% BSA), containing [$^3H$]-cholesterol-labeled acetylated low density lipoprotein (AcLDL). The [$^3H$]-cholesterol-labeled AcLDL was prepared by incubating [$^3H$]-cholesterol for 30 min at 37° C. with the AcLDL and diluted with DGGB to yield a final concentration of 50 µg/ml AcLDL with 0.33 µCi/ml [$^3H$]-cholesterol. The day after labeling, the cells were washed three times in PBS, 0.2% BSA and incubated with 0.5 ml of DGGB with or without 0.3 mM 8-Br-cAMP for 16 h (used to induce ABCA1). Cholesterol efflux to HDL or apoA-I was measured after 4 hr incubation in 0.5 ml DGGB in the presence or absence of 8-Br-cAMP. Radioactivity in a 100 µL aliquot of medium and from a hexane/isopropanol (3:2, v:v) extract from the cells were determined. The percent cholesterol efflux was calculated as the radioactivity in the medium divided by the total radioactivity (medium plus cells). Studies comparing ABCA1-dependent cholesterol efflux activity versus apoA-I $NO_2Tyr$ and ClTyr contents of HDL were performed on HDL recovered from aliquots of serum using affinity purified anti-HDL IgY gel (GenWay Biotech, San Diego, Calif.). To ensure that comparable mass of ApoA-I was applied to cells in experiments evaluating ABCA1-dependent efflux versus apoA-I $NO_2Tyr$ and ClTyr levels (FIG. 7), SDS-PAGE analyses with Coomassie blue staining of the anti-HDL precipitates was performed, revealing that >90% of the protein recovered was apoA-I. Individual subject's serum ApoA-I $NO_2Tyr$ and ClTyr contents were performed in parallel following SDS-PAGE analysis of lipoprotein recovered from immobilized anti-HDL IgY gel, transfer to PVDF and staining, and excision of the apoA-I band, followed by stable isotope dilution tandem mass spectrometry as described below.

Protein identification by mass spectrometry. Protein identifications were carried out as previously described (Kinter, M., et al., 2000, *Protein Sequencing and Identification Using Tandem Mass Spectrometry*, Willard, B. B., et al., 2003, *Analytical Chemistry*. 75:2370-2376). Briefly, bands were cut from Coomassie blue stained SDS-PAGE gels, reduced with DTT and alkylated with iodoacetamide. Protein was then digested in-gel by adding trypsin, peptides extracted, and then analyzed by capillary column HPLC-tandem mass spectrometry on an LCQDeca ion trap mass spectrometer system (ThermoFinnigan, San Jose, Calif.) equipped with a nanospray ionization source at a flow rate of 200 nL/min. Digest peptides were separated by reversed-phase capillary HPLC using a 50-µm-i.d. column with a 10-µm tip purchased from New Objective Corp. (Woburn, Mass.). The column was packed with ~6 cm of C18 packing material (Phenomenex, Torrence, Calif.) and eluted using a 45-min gradient of increasing acetonitrile (2-70%) in 50 mM acetic acid. Protein identification was performed using a data-dependent analysis that acquired both mass spectra and CID spectra in a single run (Kinter, M., et al., 2000, *Protein Sequencing and Identification Using Tandem Mass Spectrometry, Willard, B. B., et al., 2003, Analytical Chemistry*. 75:2370-2376). The search programs Sequest and Mascot were used for protein identifications. Manual sequence analyses were performed on select deuterium-enriched peptides during hydrogen-deuterium exchange mass spectrometry.

Nitrotyrosine and chlorotyrosine analyses—Protein-bound nitrotyrosine and chlorotyrosine were quantified by stable isotope dilution liquid chromatography-tandem mass spectrometry (Brennan, M. L., et al., 2002, *Journal of Biological Chemistry*. 277:17415-17427) on a triple quadrupole mass spectrometer (API 4000, Applied Biosystems, Foster City, Calif.) interfaced to a Cohesive Technologies Aria LX Series HPLC multiplexing system (Franklin, Mass.). Synthetic [$^{13}C_6$]-labeled standards were added to samples (either aliquots of serum, tissue/lesion homogenates, or bands visualized on PVDF membranes by colloidal blue stain and then excised) and used as internal standards for quantification of natural abundance analytes. Simultaneously, a universal labeled precursor amino acid, [$^{13}C_9$, $^{15}N_1$]tyrosine, was added. Proteins were hydrolyzed under argon atmosphere in methane sulfonic acid, and then samples passed over mini solid-phase C18 extraction columns (Supelclean LC-C18-SPE minicolumn; 3 ml; Supelco, Inc., Bellefone, Pa.) prior to mass spectrometry analysis. Results are normalized to the content of the precursor amino acid tyrosine, which was monitored within the same injection. Intrapreparative formation of both nitro[$^{13}C_9$, $^{15}N$]tyrosine and chloro[$^{13}C_9$, $^{15}N$]tyrosine was routinely monitored and negligible (i.e. <5% of the level of the natural abundance product observed) under the conditions employed.

Statistical Analysis. Power calculations were performed based on previously reported means and standard deviations of $NO_2Tyr$ and ClTyr in clinical studies. It was determined that at least 30 patients were needed in each group to have 80% power to detect a 40% difference in marker level. Data are presented as median (interquartile range) and significance level was set at p<0.05. Wilcoxon Rank-Sum test was used to compare levels between groups. Logistic regression was used to obtain Odds Ratio by tertiles. Pearson product-moment or Spearman-rank correlation coefficients were generated to assess the association amongst $NO_2Tyr$, ClTyr and cholesterol efflux values. Statistical analyses were performed using SPSS version 11.0 (Chicago, Ill.).

Results

Identification of Apolipoprotein A-I as a Nitrated Protein in Serum.

Figure 2:
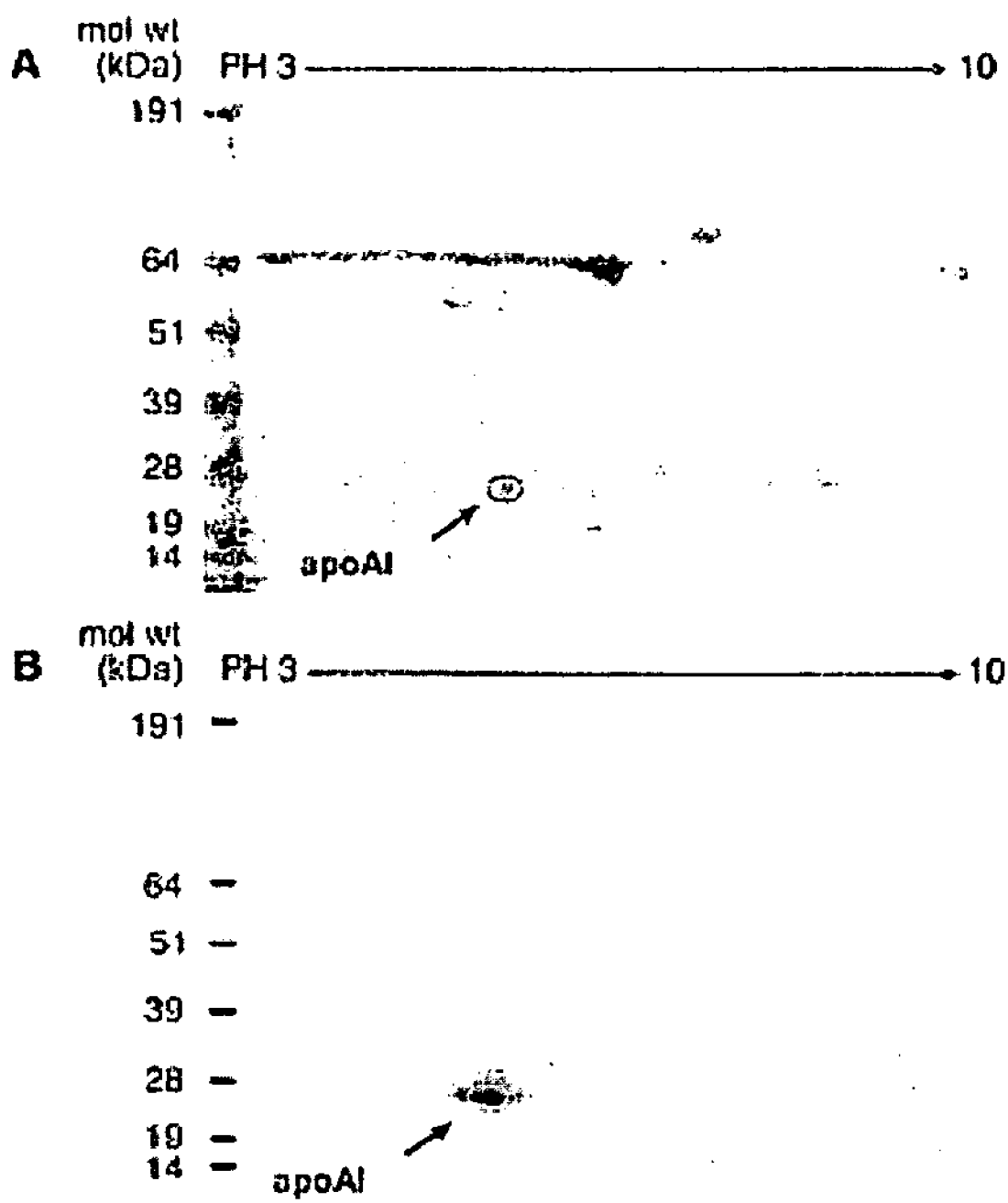
FIG. 2. Confirmation of apolipoprotein A-I as a nitrated protein by both 2-D SDS-PAGE and anti-nitrotyrosine affinity chromatography coupled to tandem mass spectrometry-based sequencing. Plasma from a subject with CVD was loaded onto an affinity matrix comprised of immobilized affinity-purified rabbit anti-nitrotyrosine polyclonal antibodies, washed with high salt, and then eluted with addition of 5 mM free nitrotyrosine, as described under Methods. (Top) Demonstration of apoA-I location on 2-D SDS-PAGE. Identity of protein was established by tandem MS sequence analysis of peptides (>95% coverage). (Bottom) The anti-nitrotyrosine eluent (5 mM nitrotyrosine) was subjected to 2-D SDS-PAGE and the presence of apoA-I confirmed by Western Blot analysis. Parallel studies using control non-immune IgG as the affinity matrix failed to bind detectable levels of apoA-I (not shown).

Serum levels of protein-bound nitrotyrosine serve as a predictor of atherosclerotic risk and burden in subjects (Shishehbor, M. H., et al., 2003, *JAMA*. 289:1675-1680), raising the question of whether nitration of specific proteins might contribute to the atherosclerotic process. As a first step in investigating this question, we sought to determine the identities of nitrated proteins in serum. Samples from patients with CVD and controls were analyzed by SDS-PAGE and visualized by both Western blot analysis using anti-nitrotyrosine antibodies, and Coomassie blue staining for proteins. Comparison of the pattern of immunoreactivity seen in the Western blot (FIG. 1, bottom panel) vs. protein staining (top panel) reveals that not all serum proteins are equally nitrated. An example of a disparity between a modest abundance vs. an extensive degree of nitration was reproducibly observed in a 29 kDa protein. This protein band was cut from the Coomassie blue-stained gel, digested with trypsin, and unequivocally identified as apoA-I (NCBI accession number 253362) based upon the detection and sequencing of >30 peptides covering 96% of the protein sequence. Further confirmation of the identity of apoA-I as a nitrated protein was obtained through passage of serum through a column comprised of immobilized antibodies to nitrotyrosine, washing the column with high salt, followed by elution with high salt supplemented with 5 mM nitrotyrosine (FIG. 2). Analysis of samples by 2-dimensional SDS-PAGE and capillary LC-tandem mass spectrometry-based sequencing confirmed apoA-I as a recovered protein (>90% coverage by LC/ESI/MS/MS). Further examination of the anti-nitrotyrosine column eluent (high salt+5 mM nitrotyrosine) by 2-D SDS-PAGE followed by Western blot analysis using antibodies to apoA-I provided additional complementary evidence of apoA-I as a nitrated protein in vivo (FIG. 2, bottom).

Demonstration of Apolipoprotein A-I as a Preferred Target of Nitration and Chlorination within Serum, as Well as in Subjects with Versus Without Cardiovascular Disease.

Given the plethora of targets within tissues like serum and the relatively short diffusion distance for a reactive nitrogen species in complex biological matrices, the apparent selective nitration of apoA-I amongst serum proteins strongly suggested the existence of an enzymatic source for NO-derived oxidants in close proximity to the lipoprotein in vivo. One likely candidate was the enzyme MPO, since recent studies have shown this enzyme both capable of catalyzing protein nitration in vivo (Brennan, M. L., et al., 2002, *Journal of Biological Chemistry*. 277:17415-17427, Zhang, R., et al., 2002, *Journal of Biological Chemistry*. 277:46116-46122, Baldus, S., et al., 2001, *Journal of Clinical Investigation*. 108:1759-1770, Gaut, J. P., et al., 2002, *Journal of Clinical Investigation*. 109:1311-1319), as well as playing a dominant role in generation of NO-derived oxidants under certain circumstances, such as within the extracellular compartment at sites of inflammation (Brennan, M. L., et al., 2002, *Journal of Biological Chemistry*. 277:17415-17427). In order to both test the hypothesis that MPO serves as a possible enzymatic catalyst for selective apoA-I nitration in vivo, as well as quantitatively assess whether apoA-I is nitrated to a greater extent within subjects with CVD, sequential patients presenting to a cardiology clinic with documented CVD (n=45) and healthy control subjects (n=44) were consented and their serum samples collected for analysis. The contents of both $NO_2Tyr$ and ClTyr were simultaneously quantified within total serum proteins, isolated apoA-I and isolated apoB-100 utilizing stable isotope dilution HPLC with on-line electrospray ionization tandem mass spectrometry (LC/ESI/MS/MS). Table 2 lists the clinical and laboratory characteristics of the subjects examined. As anticipated, patients with CVD were more likely to have known CVD risk factors including history of diabetes, hypertension, smoking, family history of CVD, and history of hyperlipidemia. Subjects with CVD also had lower LDL cholesterol levels and were more likely to be on statin therapy, features likely attributable to ascertainment bias from enrollment of CVD subjects in a cardiology clinic.

TABLE 2

Clinical and laboratory characteristics

|  | Controls (n = 44) | CVD (n = 45) | p value |
|---|---|---|---|
| Age | 44.3 ± 11.1 | 65.6 ± 8.5 | <0.001 |
| Male gender (%) | 24 (54.6) | 17 (37.8) | 0.12 |
| Diabetes (%) | 0 (0) | 24 (53.3) | <0.001 |
| Hypertension (%) | 14 (31.8) | 32 (71.1) | <0.001 |
| Smoking (%) | 22 (50.0) | 37 (82.2) | 0.001 |
| Family hx CVD (%) | 5 (11.4) | 19 (42.2) | 0.001 |
| Hx hyperlipidemia (%) | 7 (15.9) | 31 (68.9) | <0.001 |
| Statin use | 0 (0) | 28 (62.2) | <0.001 |
| TC (mg/dL) | 201 ± 33 | 165 ± 36 | <0.001 |

TABLE 2-continued

Clinical and laboratory characteristics

| | Controls (n = 44) | CVD (n = 45) | p value |
|---|---|---|---|
| HDLc (mg/dL) | 60 ± 16 | 42 ± 15 | <0.001 |
| LDLc (mg/dL) | 120 ± 34 | 91 ± 24 | <0.001 |
| TG (mg/dL) | 108 ± 54 | 171 ± 96 | <0.001 |
| Fasting Glucose (mg/dL) | 93 ± 13 | 94 ± 3 | 0.43 |

Data are presented as either percent or mean ± standard deviation as indicated.
CVD = cardiovascular disease;
HDLc = high density lipoprotein cholesterol;
Hx = history of;
LDLc = low density lipoprotein cholesterol;
TC = total cholesterol;
TG = triglyceride.

Consistent with our recent published studies (Shishehbor, M. H., et al., 2003, *JAMA*. 289:1675-1680), serum NO$_2$Tyr content was significantly increased approximately 1.5-fold (p<0.001) in subjects with CVD relative to that of healthy controls (Table 3). Similar results (2-fold increase; p=0.001 for CVD vs. controls, Table 3) were observed when analyzing the NO$_2$Tyr content of isolated apoB-100, the major protein constituent of LDL and a lipoprotein reported to bind to MPO in vitro (Carr, A. C., et al., 2000, *FEBS Letters*. 487:176-180, Yang, C. Y., et al., 1999, *Journal of Lipid Research*. 40:686-698). Remarkably, a 70-fold enrichment in NO$_2$Tyr content was noted within serum apoA-I relative to serum total proteins and isolated apoB-100. Moreover, a significant increase in NO$_2$Tyr content of apoA-I was also noted in serum from CVD vs. healthy control subjects (p=0.005; Table 3). Parallel analyses of samples for ClTyr content, a protein modification specific for MPO-catalyzed oxidation (Hazen, S. L., et al., 1999, *Methods in Enzymology* 300:88-105, Brennan, M. L., et al., 2002, *Journal of Biological Chemistry*. 277:17415-17427, Hazen, S. L., et al., 1997, *Journal of Clinical Investigation*. 99:2075-2081, Brennan, M. L., et al., 2001, *J. Clin. Invest*. 107:419-30), revealed relatively low levels within total proteins and isolated apoB-100 from serum compared to over 100-fold enrichment in ClTyr content noted within isolated apoA-I (Table 3). Further, while trends for increases in ClTyr content within subjects with CVD were noted in total protein and isolated apoB100, these differences failed to reach statistical significance. In contrast, significant increases in ClTyr content were observed within apoA-I recovered from serum (p<0.001; Table 3).

TABLE 3

Apolipoprotein A-I is a preferred target for nitration and chlorination in serum and in cardiovascular disease

| | Nitrotyrosine | | Chlorotyrosine | |
|---|---|---|---|---|
| | median(IQR) (μmol oxTyr/mol Tyr) | p value | median(IQR) (μmol oxTyr/mol Tyr) | p value |
| Section 1.01 Serum total protein | | | | |
| Control | 6.1 [3.9-7.8] | | 1.6 [0.6-2.4] | |
| CVD | 9.0 [5.7-12.9] | <0.001 | 1.9 [1.3-3.1] | 0.07 |
| apoB-100 | | | | |
| Control | 4.0 [1.3-6.9] | | 0.0 [0.0-1.9] | |
| CVD | 8.7 [5.2-12.1] | 0.001 | 1.9 [0.1-4.0] | 0.24 |

TABLE 3-continued

Apolipoprotein A-I is a preferred target for nitration and chlorination in serum and in cardiovascular disease

| | Nitrotyrosine | | Chlorotyrosine | |
|---|---|---|---|---|
| | median(IQR) (μmol oxTyr/mol Tyr) | p value | median(IQR) (μmol oxTyr/mol Tyr) | p value |
| Section 1.02 apoA-I | | | | |
| Control | 438 [335-598] | | 186 [114-339] | |
| CVD | 629 [431-876] | 0.005 | 500 [335-765] | <0.001 |

Aliquots of serum (100 ug protein) from the entire cohort from Table 1 (CVD and healthy control subjects) were either analyzed directly (for total protein) or resolved by SDS PAGE, transferred to PVDF membranes, and bands corresponding to apoA-I and apoB-100 visualized, excised, and then analyzed by stable isotope dilution LC/ESI/MS/MS, as described under Methods.
Results shown are for median and interquartile ranges of nitrotyrosine and chlorotyrosine contents of total serum protein or the indicated lipoprotein, expressed as the mole ratio of oxidized amino acid to parent amino acid, tyrosine.
The p values shown are for comparisons of NO$_2$Tyr and ClTyr content between Control and CVD groups within the corresponding indicated protein(s).
apo = apolipoprotein;
CVD = cardiovascular disease;
IQR = interquartile range.

The strength of the relationship between the content of NO$_2$Tyr and ClTyr within total proteins and isolated apoA-I from serum was further examined in the entire cohort (CVD plus controls). As shown in Table 4 (top), increasing NO$_2$Tyr content was associated with increasing frequency of CVD, as monitored in either total serum proteins or isolated apoA-I from serum. Further, comparisons between subjects with higher vs. lower levels of NO$_2$Tyr (third vs. first tertile) demonstrated approximately 6-fold increase in odds for having CVD, whether examining total proteins or isolated apoA-I from serum (Table 4, bottom). In contrast, only the ClTyr content of isolated apoA-I, and not ClTyr content of total serum proteins (or apoB-100, not shown), was associated with increasing frequency or odds of CVD within the cohort. Remarkably, subjects possessing a high (top tertile) apoA-I ClTyr content were 16-fold more likely to have CVD than those with low (bottom tertile) apoA-I ClTyr content (Table 4, bottom).

TABLE 4

Relationship between serum total protein and apolipoprotein A-I nitrotyrosine and chlorotyrosine content with cardiovascular disease prevalence

| | Frequency of CVD per Tertile | | | |
|---|---|---|---|---|
| Serum | 1 | 2 | 3 | p for trend |
| Total protein NO$_2$Tyr | 30.8% | 33.3% | 69.2% | 0.005 |
| apoA-I NO$_2$Tyr | 32.0% | 44.0% | 72.0% | 0.005 |
| 1. total protein ClTyr | 40.0% | 50.0% | 58.3% | 0.20 |
| apoA-I ClTyr | 20.0% | 48.0% | 80.0% | <0.001 |

| | Odds Ratio (95% CI) of CVD per Tertile | | |
|---|---|---|---|
| Serum | 1 | 2 | 3 |
| Total protein NO$_2$Tyr | 1.0 | 1.1 (0.4-3.6) | 5.1 (1.6-16.4) |
| apoA-I NO$_2$Tyr | 1.0 | 1.7 (0.5-5.3) | 5.5 (1.6-18.4) |

TABLE 4-continued

Relationship between serum total protein and apolipoprotein A-I nitrotyrosine and chlorotyrosine content with cardiovascular disease prevalence

| | | | |
|---|---|---|---|
| 2. total protein ClTyr | 1.0 | 1.5 (0.5-4.6) | 2.1 (0.7-6.6) |
| apoA-I ClTyr | 1.0 | 3.7 (1.1-13.0) | 16.0 (4.0-64.0) |

Displayed are (top) frequencies of cardiovascular disease prevalence within each tertile of the entire cohort; and (bottom) odds ratios and 95% confidence intervals for second and third tertiles compared to the lowest (first) tertile as predictors of CVD.
apo = apolipoprotein;
CI = confidence interval;
ClTyr = chlorotyrosine;
CVD = cardiovascular disease;
$NO_2Tyr$ = nitrotyrosine.

Demonstration of Apolipoprotein A-I as a Preferred Target of Nitration and Chlorination within Human Atherosclerotic Lesions.

Figure 3:
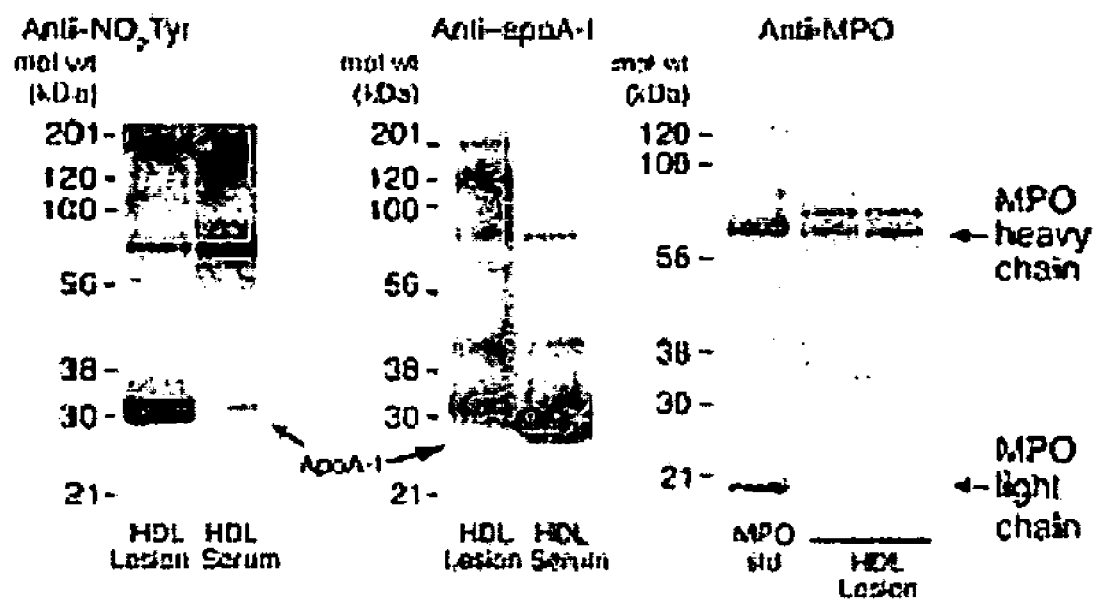
FIG. 3. Demonstration of apoA-I nitrotyrosine and MPO enrichment within HDL-like particles isolated from human atherosclerotic lesions. (Left and Center) Equal amounts of protein (40 μg per lane) from either HDL-like particles isolated from human atherosclerotic lesions (n=12 subjects, pooled), or HDL isolated from pooled plasmas from healthy donors, were analyzed by SDS-PAGE (10-20% gradient gels), transferred onto PVDF membrane, and probed using antibodies to either (left) anti-nitrotyrosine or (center) anti-apoA-I, and then visualized by brief chemiluminescence exposure, as described under Methods. (Right) Isolated human MPO standard or HDL-like particles isolated from human atherosclerotic lesions (40 ug total protein, n=12 subjects, pooled), were analyzed by SDS-PAGE (10-20% gradient gels), transferred onto PVDF membrane, probed using antibodies to human MPO, and then visualized by brief chemiluminescence exposure, as described under Methods.

To examine whether the preferential targeting of apoA-I by NO- and MPO-generated oxidants occurred within human atheroma, additional studies were performed examining total proteins, apoB-100 and apoA-I recovered from human aortic tissues. LDL-like and HDL-like particles were isolated from both normal aortic tissues and atherosclerotic tissues by differential buoyant density centrifugation, and then confirmed to be enriched both in cholesterol and the appropriate apolipoprotein preparation by Western analyses using polyclonal antibodies to either apoB-100 or apoA-I, as described under "Methods". FIG. 3 (left) illustrates the further enrichment of $NO_2Tyr$ content within HDL-like particles isolated from human atherosclerotic lesions, compared to analysis of a comparable amount of isolated HDL from peripheral blood. The majority of apoA-I recovered within HDL-like particles from atherosclerotic lesions was monomeric (FIG. 3, center). More quantitative assessments of $NO_2Tyr$ and ClTyr contents of apoA-I recovered from normal aortic and lesion tissues relative to that observed in aortic and lesion total proteins and apoB-100 were obtained by stable isotope dilution LC/ESI/MS/MS analyses, the results for which are shown in Table 5. Of note, the contents of $NO_2Tyr$ and ClTyr within total proteins, apoB-100 and apoA-I recovered from normal aortic tissues and human atherosclerotic lesions were higher than that observed in serum (compare Tables 3 versus 5), suggesting protein modification by NO- and MPO-generated oxidants preferentially occurs within the artery wall, particularly within atherosclerotic lesions, compared to the intra-vascular (blood) compartment. As was observed within serum and the serum-derived isolated lipoproteins, the contents of both $NO_2Tyr$ and ClTyr in lesion apoA-I demonstrated a dramatic selective enrichment relative to lesion total proteins and lesion apoB-100 (Table 5). Similarly, higher levels are observed within total proteins and the isolated lipoproteins from diseased vs. normal vascular tissues.

TABLE 5

Apolipoprotein A-I is a preferred target for nitration and chlorination within human aortic atherosclerotic lesions

| | Nitrotyrosine | | Chlorotyrosine | |
|---|---|---|---|---|
| | Median(IQR) (μmol oxTyr/mol Tyr) | p value | Median(IQR) (μmol oxTyr/mol Tyr) | P value |
| Section 1.03 Normal | | | | |
| total protein | 55 [24-143] | | 63 [25-128] | |
| apoB-100 | 97 [43-222] | 0.57 | 49 [21-121] | 0.93 |
| Section 1.04 apoA-I | 401 [185-637] | <0.001 | 678 [299-1,311] | <0.001 |
| Section 1.05 Lesion | | | | |
| total protein | 108 [51-346] | | 232 [111-431] | |
| apoB-100 | 255 [91-480] | 0.67 | 318 [59-385] | 0.92 |
| Section 1.06 apoA-I | 2,340 [1,665-5,050]* | <0.001 | 3,930 [1,679-7,005]* | <0.001 |

Specimens of normal human aorta (n = 10 subjects) and human aortic atherosclerotic tissues (n = 22 subjects) were stripped of adventia, and then, pulverized into a powder in stainless steel mortar and pestle at liquid nitrogen temperatures, and the contents of nitrotyrosine andchlorotyrosine analyzed by stable isotope dilution LC/ESI/MS/MS, as described under Methods. Total protein content of biomarkers was ascertained using powdered human vascular tissue. The contents of oxidized amino acids within normal aortic and atherosclerotic lesion - derived apoB-100and apoA-I were assessed following isolation of LDL-like and HDL-like particles from powdered vascular tissues by sequential buoyant density centrifugation, further resolving by SDS PAGE, transfer to PVDF membranes, and then bands corresponding to apoA-I and apoB-100visualized, excised, and analyzed by stable isotope dilution LC/ESI/MS/MS, as described under Methods. Results shown are for median and interquartile ranges of nitrotyrosine and chlorotyrosine contents of normal aortic and lesion total protein or the indicated lipoproteins,expressed as the mole ratio of oxidized to parent amino acid, tyrosine. The p values shown are for comparisons of nitrotyrosine or chlorotyrosine content in the indicated isolated lipoproteins from human normal aortic and atherosclerotic lesions vs. the corresponding content observed innormal or lesion aortic tissue total proteins.
*P < 0.001 for comparison of lesional apoA-I versus normal aortic tissue apoA-I.

Demonstration that Myeloperoxidase Binds Directly to Apolipoprotein A-I.

Figure 4:
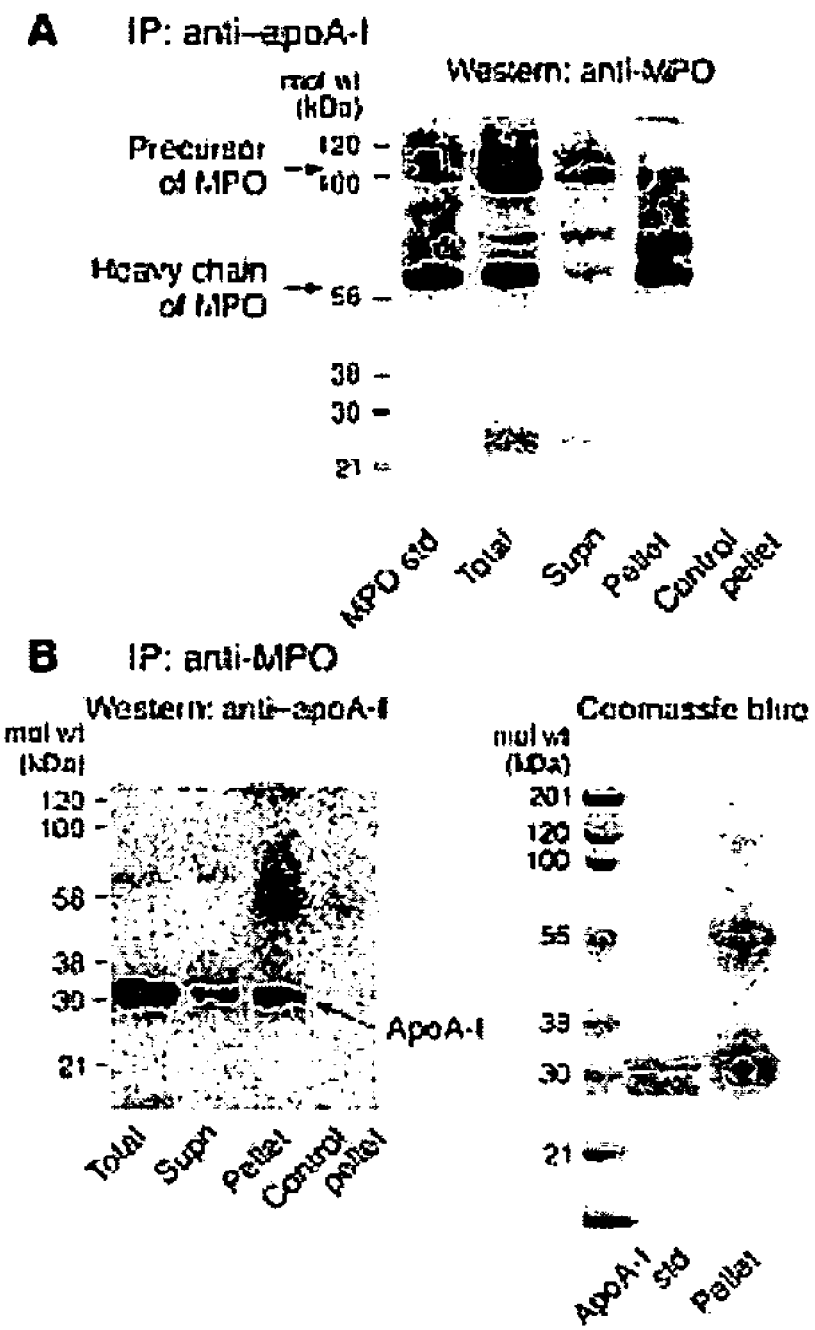
FIG. 4. Co-immunoprecipitation of MPO and apoA-I in plasma. (Panel A) ApoA-I immunoprecipitation (IP) of plasma, followed by MPO Western blot (10-20% SDS-PAGE). (Panel B) MPO IP of plasma, followed by apoA-I Western blot (10-20% SDS-PAGE) (left) or Coomassie blue staining (right). The MPO Western blot (Panel A) was probed with rat anti human MPO, and includes in the first lane isolated human MPO as standard. The anti-MPO antibody used predominantly recognizes the heavy chain of MPO, and thus highlights both heavy chain and precursor protein forms of MPO. The apoA-I Western blot (Panel B) was probed with goat anti human apoA-I. For each Western, the lanes were loaded with 10 □g of protein from plasma, the IP supernatant, and the specific and control immune complexes recovered from the IP pellets, in the indicated sequential order.

The selective enrichment of $NO_2Tyr$ and ClTyr, a specific oxidative modification for MPO (Hazen, S. L., et al., 1999, *Methods in Enzymology* 300:88-105, Brennan, M. L., et al., 2002, *Journal of Biological Chemistry*. 277:17415-17427, Hazen, S. L., et al., 1997, *Journal of Clinical Investigation*. 99:2075-2081, Brennan, M. L., et al., 2001, *J. Clin. Invest*. 107:419-30), within apoA-I, whether recovered from serum or within human atherosclerotic vessels, suggests a possible (patho)physiologic association between apoA-I and MPO in vivo. Independent support for such an association is the observed strong and statistically significant correlation ($R=0.58$, $p<0.001$) noted between ClTyr and $NO_2Tyr$ contents of apoA-I, consistent with a significant common pathway for formation (i.e. MPO). To directly test the hypothesis that MPO interacts with apoA-I, cross immunoprecipitation studies were performed within plasma from a healthy donor that was supplemented with purified human MPO. Remarkably, antibodies to apoA-I efficiently pulled down MPO in plasma, and conversely, antibodies to MPO efficiently extracted apoA-I from plasma. Parallel control studies using immobilized non-immune IgG preparations failed to precipitate either MPO or apoA-I (FIG. 4). Further analysis of the proteins recovered from plasma following incubation with immobilized anti-MPO antibodies by SDS-PAGE and Coomasie blue staining revealed that apoA-I was a major protein recovered (FIG. 4B, Right). Finally, a remarkable finding was that MPO was identified as an HDL-associated protein within human atheroma following the multi-step buoyant density isolation procedure for HDL-like particle recovery from atherosclerotic lesions (FIG. 3, right). Collectively, these results strongly suggest that MPO directly associates with apoA-I within the artery wall, facilitating selective oxidative modification through reactive halogen and nitrogen species.

The interaction of MPO and HDL was examined more closely using hydrogen/deuterium exchange coupled to mass spectrometry to identify potential MPO—apoA-I contact(s) sites. The hydrogen/deuterium exchange method is based on monitoring the ability of backbone amide protons to exchange with the solvent as a measure of solvent accessibility—a process which occurs readily at neutral pH, but which can be slowed 10-orders of magnitude at acidic pH (pH 2) (Zhang, Z., et al., 1993, *Protein Science*. 2:522-531, Woods, V. L., Jr., et al., 2001, *Journal of Cellular Biochemistry Supplement* 37:89-98). By pre-exchanging the labile backbone hydrogens to deuterium, the solvent accessible sites on the protein are labeled in a manner that allows back exchange with hydrogen to be monitored by mass spectrometry (Zhang, Z., et al., 1993, *Protein Science*. 2:522-531, Woods, V. L., Jr., et al., 2001, *Journal of Cellular Biochemistry Supplement* 37:89-98). When combined with pepsin digestion of the protein and micro-LC MS analysis, the degree of back exchange can be sensitively and specifically measured within individualized peptic peptides, each of which serves as an intrinsic probe of protein-protein interactions spanning the entire protein sequence. Thus, sites of protein-protein contact, or attendant conformational alterations that alter solvent accessibility during protein-protein interactions, may be sensitively and specifically evaluated.

Figure 5:
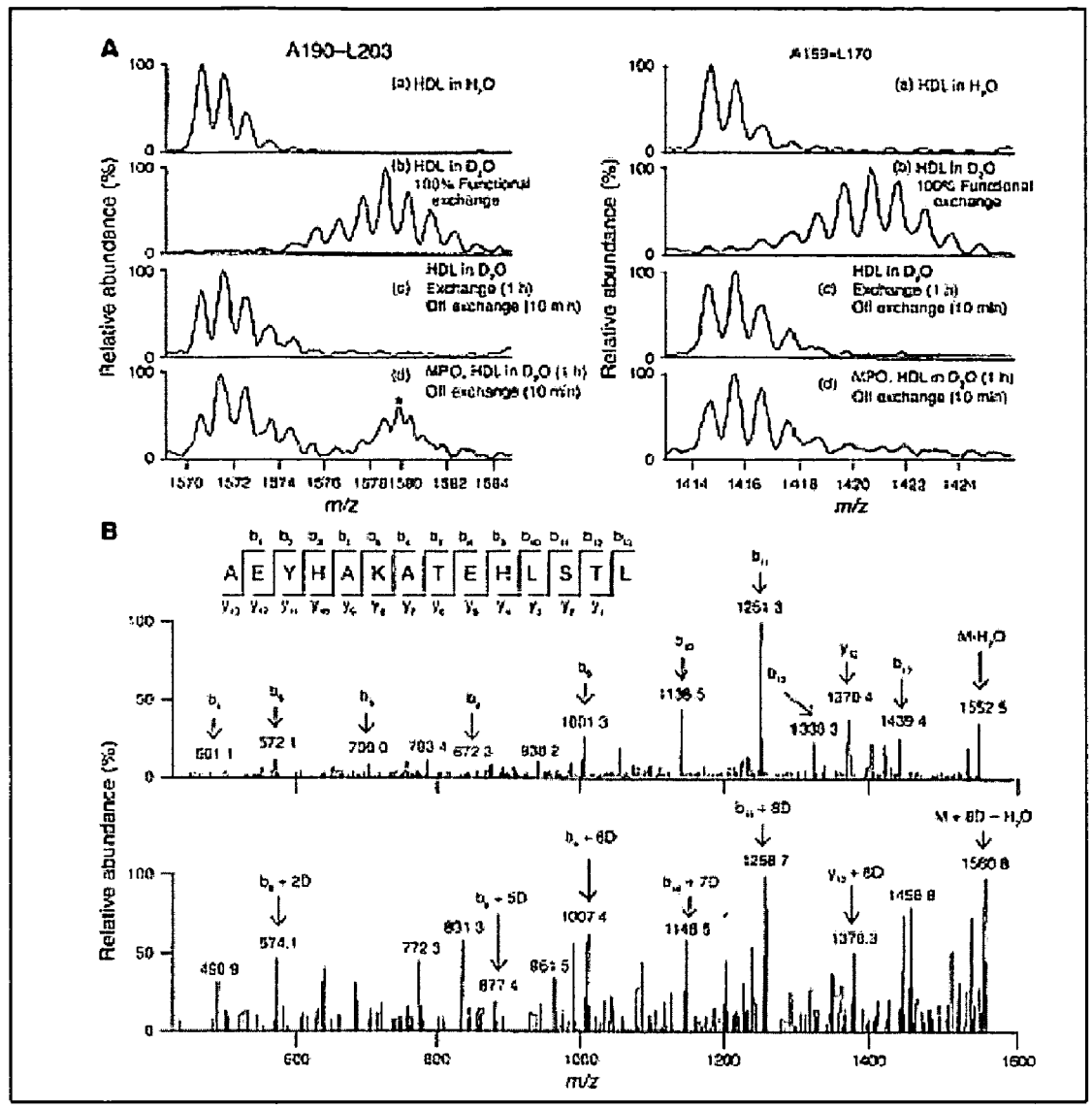
FIG. 5. Demonstration of an interaction between myeloperoxidase and apoA-I using hydrogen→ deuterium exchange tandem mass spectrometry. Exchangeable protons on HDL and human MPO were each deuterium-labeled by mixing in $D_2O$ containing $ND_4OAc$, pD 7.0 at room temperature for 1 h. The deuterated HDL was combined with either deuterated MPO or additional deuterium buffer and incubated for 1 h at room temperature to allow binding. Samples were diluted 25-fold into $NH_4OAc$, pH 7.0 for 10 minutes for back (off)-exchange before quenching by rapidly cooling on ice/methanol bath and adding TFA to reduce the pH to 2. Proteins were digested with immobilized pepsin and then samples were immediately injected for analysis by HPLC-MS as described under Methods. The different spectra shown correspond to various stages in the hydrogen/deuterium-exchange experiment. (Panel A) ApoA-I isotopic clusters shown are for either the (Left) MPO binding peptide A190-L203, or for a (Right) negative control peptide, L159-L170. For each, spectra A and B contain peptide isotopic clusters before and after deuterium labeling, respectively. Spectra C and D contain deuterium-labeled peptide cluster after back (off) exchange with hydrogen in the absence (C) and presence (D) of MPO binding, respectively. The peptide isotopic cluster indicated by the asterisk represents a non back-exchanged component of the A190-L203 isotope cluster due to inaccessibility of this region of apoA-I to solvent in the presence of MPO. Results shown are representative of 4 independent sets of hydrogen/deuterium exchange experiments monitoring reactions between isolated HDL and human MPO. (Panel B) Sequence confirmation of the identified peptic peptides was achieved by tandem mass spectrometry. The CID spectra and fragmentation analysis of the unlabeled and deuterium-labeled peptic peptide A190-L203 are illustrated (SEQ ID NO:2).

During reactions of MPO with HDL, we analyzed 22 peptic peptides covering 95% of apoA-I and found only one peptide, corresponding to a portion of helix 8 (A190-L203), that MPO protected from H/D-exchange (FIG. 5, top left, spectrum D). For these experiments, exchangeable protons on HDL and MPO were deuterated by separate incubations of each in $D_2O$ buffer at neutral pD and 37° C., followed by mixing of MPO and HDL in the same $D_2O$ buffer for 1 h. The reaction mixture was then diluted with >20-fold excess $H_2O$ buffer (pH 7.0, 37° C.) to allow the back (off) exchange (t=10 min) of deuterium with protons from solvent accessible sites on the proteins. Exchange was quenched by acidification and immersion into ice/methanol bath (pH 2.5, −10° C.), and then samples analyzed by pepsin proteolysis and reverse phase HPLC-tandem mass spectrometry. The different spectra shown in FIG. 5 (top left) show the isotopic cluster of the A190-L203 peptide of apoA-I at various stages in the hydrogen/deuterium—exchange experiment. Spectra A and B contain the peptide isotopic cluster before and after deuterium labeling, respectively; whereas spectra C and D contain the deuterium-labeled peptide cluster after back (off) exchange with hydrogen in the absence (C) and presence (D) of MPO binding, respectively. Protection of peptide A190-L203 from the back exchange is seen in the deuterated isotope cluster centered at m/z 1578.7 in the mixed MPO/HDL sample shown (FIG. 5, top left, spectrum D). In the absence of MPO (top panel, spectrum C), nearly complete back exchange is observed. For illustrative purposes, a parallel set of data for peptide L159-L170, a negative control peptide whose behavior is representative of all other peptides monitored, is also shown. Note that the leftward shift in isotopic cluster from higher m/z for this peptide during off exchange from $D_2O \rightarrow H_2O$ is complete in the presence of MPO (top right, spectra D and C are comparable), whereas a residual population of the A190-L203 peptides retained a higher m/z during the off exchange experiment in the presence of MPO (top left, spectra D and C are not comparable). Peptide identities were confirmed by sequence analysis, demonstrating incorporation of deuterium into the exchangeable peptide hydrogens, as shown for both deuterium-labeled and unlabeled forms of A190-L203 (FIG. 5, bottom panel). Further confirmation of the ApoA-I peptide A190-L203 as a probable MPO interactions site was obtained in independent hydrogen deuterium exchange studies monitoring MPO interactions with isolated human apoA-I in lipid disks (reconstituted human apoA-I in POPC—data not shown). Again, with nearly complete peptic peptide mapping (>90% coverage) of apoA-I, peptide A190-L203 was the only one protected from deuterium back exchange in the presence versus absence of MPO.

Exposure of Either HDL or apoA-I to (Patho)Physiologic Levels of MPO-Generated Nitrating or Chlorinating Oxidants Results in Selective Inhibition in ABCA1 Dependent Cholesterol Efflux from Macrophages.

We next examined if exposure of either HDL or apoA-I to physiologic levels of MPO-generated oxidants alters the cholesterol efflux capabilities of the lipoprotein. Both HDL and apoA-I (lipid-free) were individually incubated with the $MPO/H_2O_2/NO_2^-$ system (protein nitration conditions), or the $MPO—H_2O_2—Cl^-$ system (protein chlorination conditions), and then both ABCA1-dependent and independent cholesterol efflux acceptor activities were measured by incubation with cholesterol-loaded murine macrophage RAW264.7 cells in the presence and absence of pretreatment with 8Br-cAMP. In the absence of 8Br-cAMP treatment, RAW264.7 cells do not express an appreciable level of ABCA1, and thus like fibroblasts from Tangier disease subjects, these cells support cholesterol efflux to HDL via ABCA1-independent mechanisms, but almost no cholesterol efflux to apoA-I (Remaley, A. T., et al., 1997, *Arteriosclerosis, Thrombosis & Vascular Biology*. 17:1813-1821, Takahashi, Y., et al., 2000, *Biochimica et Biophysica Acta*.

Figure 6:
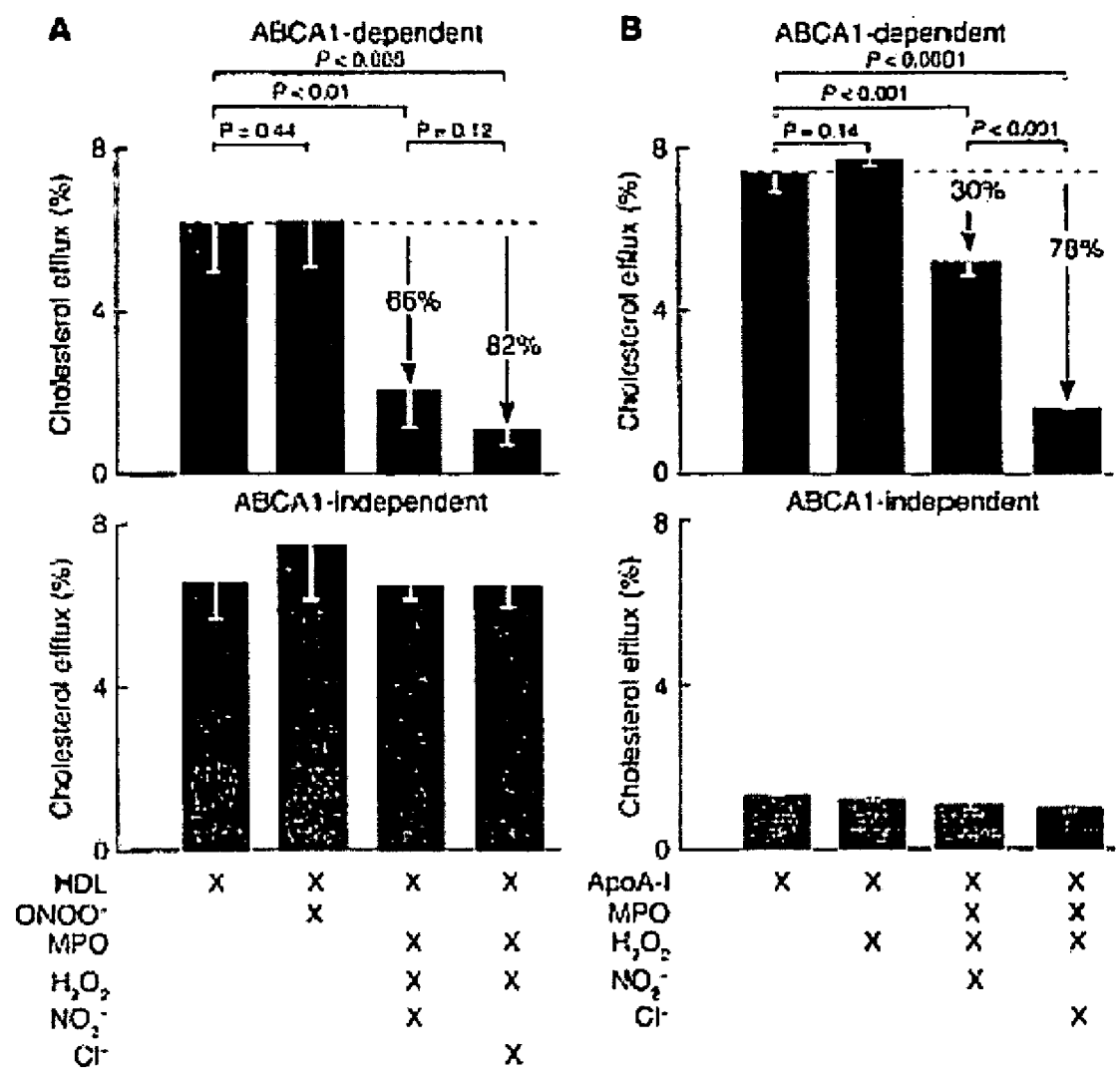
FIG. 6 Myeloperoxidase-generated reactive halogen and reactive nitrogen species inhibit ABCA1-dependent cholesterol efflux functions of HDL. HDL (Panel A) or apoA-I (Panel B) were individually modified by either $ONOO^-$ (100 μM), the $MPO-H_2O_2$—$NO_2^-$ system (100 μM $H_2O_2$), or the $MPO-H_2O_2$—$Cl^-$ system (100 μM $H_2O_2$), as described under Methods. Modified HDL or apoA-I preparations were then incubated with cholesterol-loaded murine macrophage RAW264 cells in the presence or absence of 8Br-cAMP pretreatment, and ABCA1-dependent (top) and independent cholesterol efflux (bottom) quantified as described under Methods. Note that MPO-generated nitrating and chlorinating oxidants both selectively inhibited ABCA1-dependent cholesterol efflux. In marked contrast, exposure of HDL or apoA-I to $ONOO^-$ failed to influence HDL cholesterol efflux functions of the lipoprotein.

1492:385-394, Chen, W., et al., 2000, *Journal of Biological Chemistry*. 275:30794-30800, Smith, J. D., et al., 1996, *Journal of Biological Chemistry*. 271:30647-30655). 8Br-cAMP treatment of RAW264.7 cells induces ABCA1 mRNA and protein, and thus like fibroblasts from control subjects, these cells support ~2-fold higher levels of cholesterol efflux to HDL and significant levels of cholesterol efflux to lipid-free apoA-I (Remaley, A. T., et al., 1997, *Arteriosclerosis, Thrombosis & Vascular Biology*. 17:1813-1821, Takahashi, Y., et al., 2000, *Biochimica et Biophysica Acta*. 1492:385-394, Smith, J. D., et al., 1996, *Journal of Biological Chemistry*. 271:30647-30655, Takahashi, Y., et al., 1999, *Proceedings of the National Academy of Sciences of the United States of America*. 96:11358-11363). Incubation of either HDL or lipid-free apoA-I with the complete MPO-generated nitrating or chlorinating oxidant systems resulted in significant decreases in ABCA1-dependent cholesterol efflux, without altering ABCA1-independent cholesterol efflux (FIG. 6). Analysis of the oxidatively modified forms of HDL by SDS-PAGE and protein silver-staining revealed that apoA-I remained predominantly intact, with no evidence of fragmentation, and only modest increases in cross-linked forms of apoA-I following exposure to the MPO-generated chlorinating and nitrating oxidants. In all cases, inhibition in ABCA1-dependent cholesterol efflux was only observed in the presence of all components of the complete system (MPO, $H_2O_2$ and co-substrate $NO_2^-$ or $Cl^-$), but not in the absence of any one component, or in the presence of hydrogen peroxide alone (data not shown). Remarkably, incubation of HDL with comparable levels of peroxynitrite (100 μM) failed to decrease the capacity of HDL to act as a cholesterol acceptor by either ABCA1-dependent or independent pathways, despite nitration of the apoA-I as monitored by LC/ESI/MS/MS (FIG. 6). The loss of ABCA1-dependent efflux for both MPO-modified HDL and isolated apoA-I is consistent with protein modification, rather than lipid modification, causing the effect.

Correlation between Serum apoA-I Content of Nitrotyrosine and Chlorotyrosine with Impairment in ABCA1 Dependent Cholesterol Efflux Activity in Circulating Human HDL.

Figure 7:
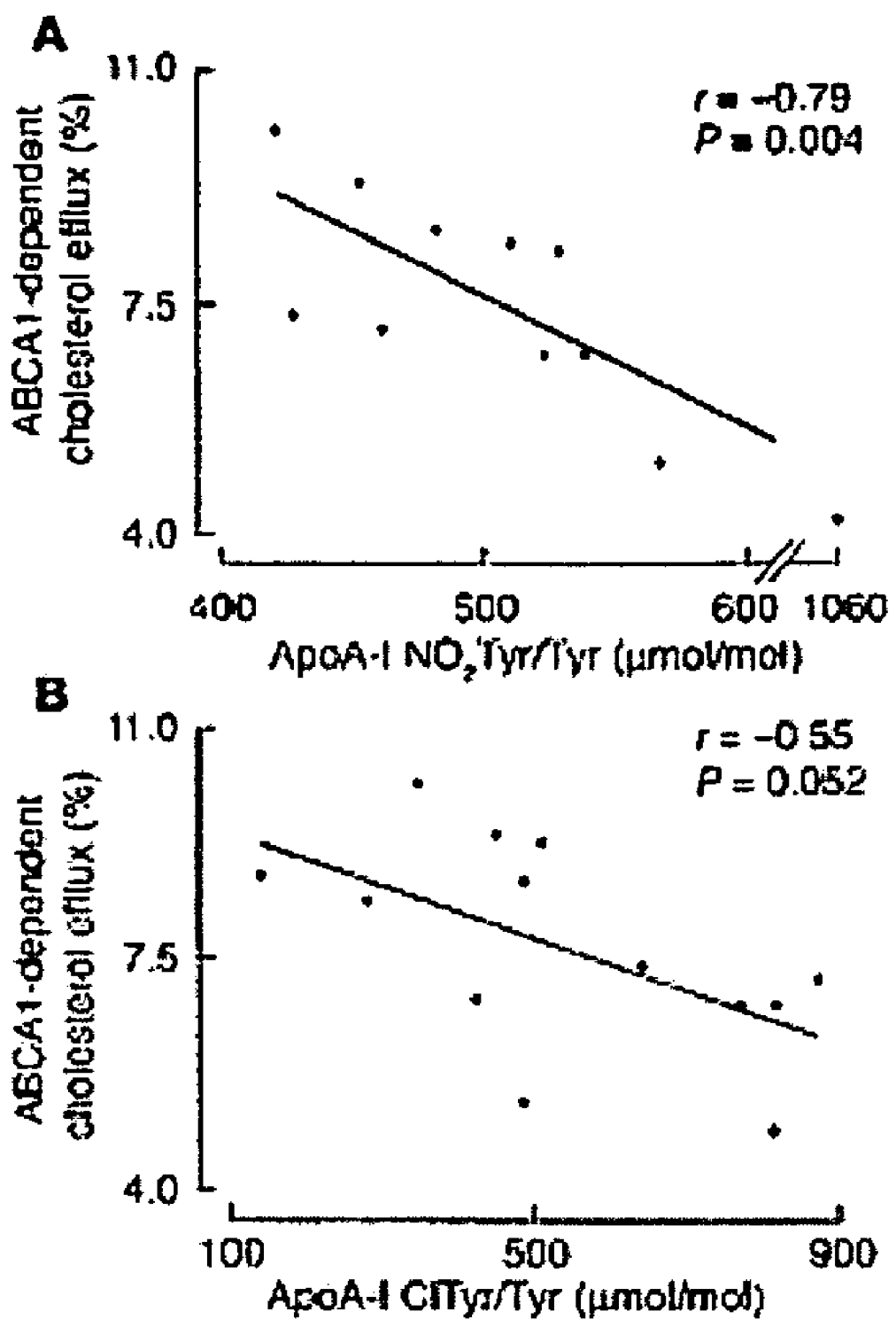
FIG. 7 Correlation between functional impairment in ABCA1-dependent cholesterol efflux activity and apoA-I content of nitrotyrosine and chlorotyrosine. HDL was immunoprecipitated from serum of consecutive Preventive Cardiology Clinic patients. ABCA1-specific cholesterol efflux activity in 5 ug apoA-I was then quantified using cholesterol-laden murine macrophages as described under Methods. In parallel, the content of apoA-I nitrotyrosine (top panel) and chlorotyrosine (bottom panel) were determined by stable isotope dilution tandem mass spectrometry as described under Methods.
Figure 8:
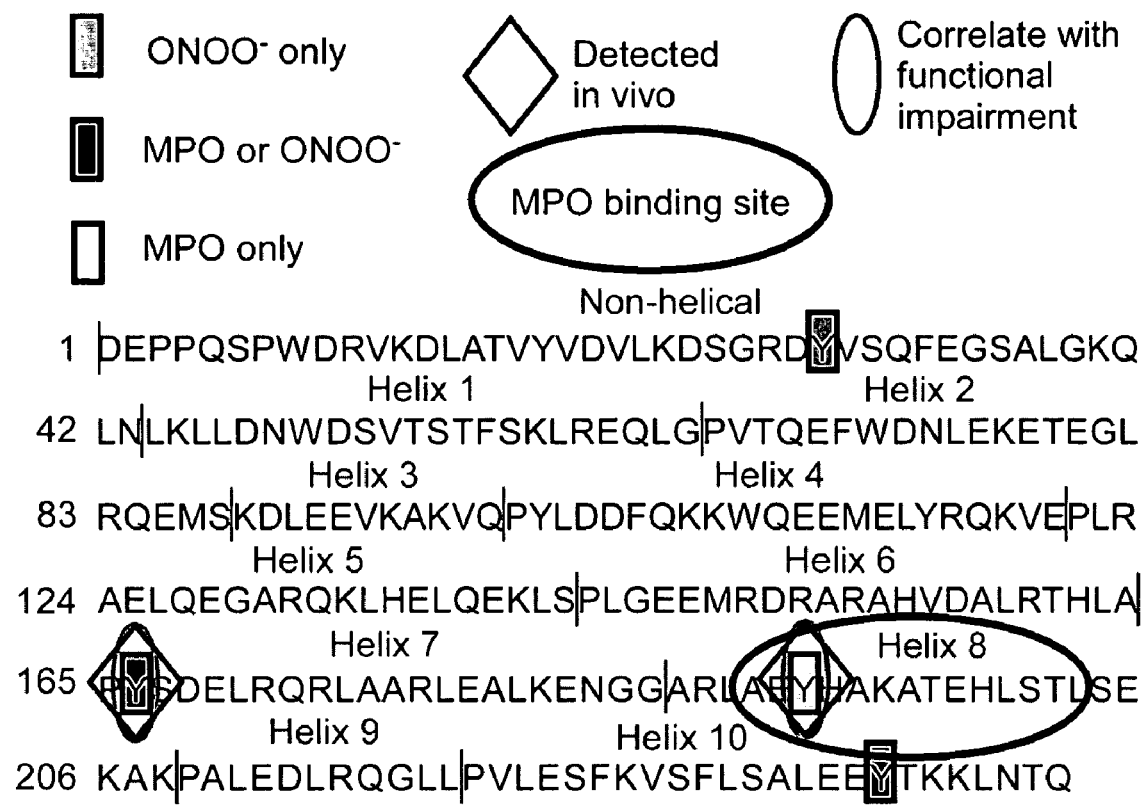
FIG. 8 Amino acid sequence, SEQ ID NO. 1, of mature apoA-1, i.e., apoA-1 minus the signal sequence. (NCBI Accession No. 229513) and the location of the MPO binding site.

We would ideally like to ascertain if MPO-catalyzed oxidative modification of apoA-I within the artery wall contributes to impairment in cholesterol efflux function of the lipoprotein in atherosclerotic lesions versus normal vessels. However, practical limitations in the amount of diseased, and especially normal, human aortic tissues obtainable precluded this examination. We therefore performed a separate clinical study to explore the in vivo functional relevance of apoA-I oxidative modification on the intrinsic cholesterol efflux activity of the circulating high density lipoprotein particle. HDL was recovered by immuno-affinity chromatography from sequential subjects, and then ABCA1-dependent cholesterol efflux activity of a fixed mass of apoA-I was determined, and in parallel, the content of apoA-I $NO_2Tyr$ and ClTyr measured, as described in Methods. Remarkably, strong and significant inverse correlations were noted for both apoA-I $NO_2Tyr$ and ClTyr levels, with higher indices of apoA-I oxidative modification correlating with greater impairment in ABCA1 dependent cholesterol efflux activity from cholesterol laden macrophages (FIG. 7).

Discussion

A growing body of evidence supports a role for inflammation and oxidative processes in cardiovascular disease pathogenesis (Chisolm, G. M., et al., *Free Radical Biology & Medicine*. 28:1815-1826. Lusis, A. J. 2000, *Nature*. 407:233-241, Navab, M., et al., 2002, *Current Opinion in Lipidology*. 13:363-372, Podrez, E. A., et al., 2000, *Free Radical Biology & Medicine*. 28:1717-1725, Heinecke, J.W. 2003, *American Journal of Cardiology*. 91:12A-16A, Boullier, A., et al., 2001, *Annals of the New York Academy of Sciences* 947:214-222). Classically, the "Oxidation Hypothesis" of atherosclerosis has predominantly focused upon the role of oxidation in the modification of LDL and phospholipids, generating pro-atherogenic species capable of promoting cholesterol deposition, foam cell formation, and proliferation of an inflammatory phenotype. However, over the past few years, evidence has accrued supporting the notion that HDL that is "dysfunctional" through oxidative modification may also play an important role in the development of atherosclerosis, and that detection of such "pro-inflammatory" HDL may be a useful marker for gauging susceptibility to atherosclerosis in subjects (Navab, M., et al., 2002, *Current Opinion in Lipidology*. 13:363-372, Navab, M., et al., 2001, *Arteriosclerosis, Thrombosis & Vascular Biology*. 21:481-488, Ansell B. J., et al., 2003, *Circulation* 108:2751-2756, Navab, M., et al., 2000, *Journal of Lipid Research*. 41:1481-1494, Navab, M., et al., 2001, *Circulation*. 104:2386-2387, Navab, M., et al., 2001, *Journal of Lipid Research*. 42:1308-1317). Despite these new insights linking oxidation and impaired HDL function with atherosclerosis, direct demonstration of the pathways that participate in HDL oxidation in vivo have not yet been reported.

The present studies provide both the first direct evidence of apoA-I, the major protein constituent of HDL, as a preferential target for nitration and chlorination in the artery wall, as well as a potential mechanism(s) for generation of a pro-atherogenic form of HDL. The remarkable selective enrichment in apoA-I $NO_2Tyr$ and ClTyr content observed both within human atherosclerotic lesions and the systemic circulation strongly supports the notion that NO-derived oxidants and MPO-catalyzed reactions selectively target the lipoprotein for oxidative modification. We observed a combined ox-amino acid (ox-AA) content of 5,500 μmol ox-AA/mol Tyr within lesional apoA-I (Table 4). Given there are 7 tyrosine residues per apoA-I and up to 4 apoA-I molecules per HDL particle, we calculate that on average, approximately 15% of the HDL-like particles recovered from human aortic lesions possess at least one oxidative modification (i.e. 5.5 ox-AA/$10^3$ Tyr×7 Tyr/apoA-I×4 apoA-I/HDL particle=15.4%). If one looks a the top quartile values, which demonstrated a combined ox-AA content ranging between 10,000 to 25,000 μmol ox-AA/mol Tyr, then a remarkable 28% to 50% of lesional HDL in this top quartile possess either a ClTyr or a $NO_2Tyr$ residue. Since MPO, HOCl-modified proteins, and apoA-I all co-localize within the protected environment of the subendothelial compartment, it is not hard to imagine that this number may be even higher in some locations. While the selective enrichment of MPO-generated oxidation products was most pronounced within circulating HDL of individuals with CVD and human atherosclerotic lesions, marked enrichment was also noted within apoA-I recovered from both serum of healthy subjects and transplant donor aortic tissues, suggesting a potential physiologic anti-inflammatory/anti-oxidant role for apoA-I binding of MPO and scavenging of MPO-generated oxidants. Whether the MPO-catalyzed oxidation of apoA-I occurs within the artery wall, or within the circulation, followed by selective deposition of the modified lipoprotein within the artery wall, cannot be determined from the present studies. Such high levels of modification, however, strongly argue for the oxidation to occur within a protected environment, such as the subendothelial compartment, where scavengers of MPO-generated oxidants might be more easily depleted.

Another remarkable finding is that both in vitro and in vivo studies demonstrate accompanying functional impairment in ABCA1-dependent cholesterol efflux from cholesterol-laden macrophages with increasing levels of oxidation of apoA-I, suggesting that oxidative processes catalyzed by MPO may participate in the development of "dysfunctional" or "pro-inflammatory" forms of HDL. The involvement of MPO as an enzymatic catalyst in the selective oxidative modification of apoA-I through both nitration and halogenation reactions is supported by multiple lines of evidence, including: (i) a dramatic enrichment in both ClTyr, a specific product of MPO, and $NO_2Tyr$, a product generated by MPO, in apoA-I recovered from both human atheroma and serum relative to both apoB-100 and total proteins from lesions and serum, respectively; (ii) the finding that MPO binds to apoA-I in HDL within plasma and serum based upon both co-immunoprecipitation studies and visualization of a probable site of apoA-I contact with MPO using hydrogen-deuterium exchange mass spectrometry; (iii) the observation that the ClTyr and $NO_2Tyr$ content of apoA-I show a remarkable statistical correlation (R=0.58, p<0.001), consistent with a significant common enzymatic source; and (iv) the co-purification of MPO with HDL-like particles recovered from human atherosclerotic lesions.

Several studies have reported functional alterations to HDL-mediated cholesterol efflux following oxidative modification in vitro; however, the impact of oxidation on cholesterol efflux functions have been contradictory, with decreased (Nagano, Y., et al., 1991, *Proceedings of the National Academy of Sciences of the United States of America*. 88:6457-6461, Panzenboeck, U., et al., 1997, *Journal of Biological Chemistry*. 272:29711-29720, Bergt, C., et al., 2001, *European Journal of Biochemistry*. 268: 3523-3531), no change (Graham A, et al., 1998, FEBS Lett; 431:327-332), and increased (Wang, W. Q., et al., 1998, *Journal of Biological Chemistry*. 273:17391-17398, Panzenbock, U., et al., 2000, *Journal of Biological Chemistry*. 275:19536-19544) rates of efflux reported. Perhaps the best evidence thus far reported has focused upon ex-vivo oxidatively cross-linked forms of apoA-I, which are reported to have enhanced efflux functional capacity in vitro, and the ability to attenuate lesion development when infused in an animal model of atherosclerosis (Panzenbock, U., et al., 2000, *Journal of Biological Chemistry*. 275:19536-19544). Despite these studies, direct examination of the relevant forms of oxidative modification that are operational within apoA-I in the artery wall had yet to be reported. Further, while enrichment of $NO_2Tyr$ and ClTyr in human atherosclerotic lesions was well known from both immunohistochemical and mass spectrometry-based studies (Leeuwenburgh, C., et al., 1997, *Journal of Biological Chemistry*. 272:1433-1436, Beckmann, J. S., et al., 1994, *Biological Chemistry Hoppe-Seyler*. 375:81-88, Hazen, S. L., et al., 1997, *Journal of Clinical Investigation*. 99:2075-2081), and co-localization of immunostaining for both apoA-I and HOCl-modified proteins within human atheroma have been reported (Marsche, G., et al., 2002, *Journal of Biological Chemistry*. 277:32172-32179), the present study is the first to directly demonstrate MPO-catalyzed oxidative modifications to apoA-I in vivo. The present studies are also the first to demonstrate that: (i) a strong correlation exists between serum apoA-I $NO_2Tyr$ and ClTyr content and CVD risk; and (ii) a strong correlation exists between serum HDL $NO_2Tyr$ and ClTyr content in subjects and the intrinsic ABCA1-mediated cholesterol efflux function of the lipoprotein particle.

Despite the many links between oxidation and atherosclerosis, it should be noted that the "Oxidation Hypothesis" of atherogenesis has come under intense scrutiny of late due to the failure of several large-scale prospective "antioxidant" intervention trials to demonstrate clinical benefit (reviewed in Wang, W. Q., et al., 1998, *Journal of Biological Chemistry*. 273:17391-17398, Panzenbock, U., et al., 2000, *Journal of Biological Chemistry*. 275:19536-19544, Marsche, G., et al., 2002, *Journal of Biological Chemistry*. 277: 32172-32179, Pryor, W. A. 2000, *Free Radic Biol Med*. 28(1):141-64. Review, Steinberg, D., et al., 2002, *Circulation* 105(17):2107-11, Vivekananthan D P, et al., *Lancet*. 361(9374):2017-23). While many have interpreted these negative results as an indictment of the Oxidation Hypothesis, direct demonstration of antioxidant action following supplementation in subjects was not shown in these trials. Remarkably, many of the oxidation pathways known to be operative in human atheroma, including those mediated by MPO-catalyzed halogenation and NO-derived oxidants, are not efficiently inhibited by α-tocopherol (Podrez, E. A., et al., 2000, *Free Radical Biology & Medicine*. 28:1717-1725, Podrez, E. A., et al., 1999, *Journal of Clinical Investigation*. 103:1547-1560, Hazell, L. J., et al., 1997, *FEBS Lett*. 414:541-544, Savenkova M L, et al., 1994, *J Biol. Chem*. 269:20394-20400, Rubbo H, et al., 2000, *J Biol. Chem*. 275:10812-8). Further, in many studies "antioxidant" vitamins like α-tocopherol and ascorbate have been shown to either have no effect on systemic measures of oxidant stress, or even to promote oxidation by either acting as a phase transfer catalyst for radical species (e.g. tocopherol-mediated peroxidation) or allowing redox-active transition metal ions to catalytically cycle (Upston, J. M., et al., 1999, *FASEB J*. 13:977-94, Lee, S. H., et al., 2001, *Science* 292:2083-6. Meagher, E. A., et al., 2001, *JAMA*. 285:1178-82). Given our recent demonstrations of systemic reductions in total protein $NO_2Tyr$ and ClTyr contents of subjects receiving statin therapy (Shishehbor, M. H., et al., 2003, *JAMA*. 289:1675-1680, Shishehbor, M. H., et al., 2003, *Circulation*. 108:426-431), it is tempting to speculate that apoA-I $NO_2Tyr$ and ClTyr contents may also serve as clinically useful tools for both CVD risk stratification strategies, as well as for monitoring the anti-inflammatory and anti-oxidant actions of statins and other therapies.

Epidemiological studies consistently demonstrate an inverse correlation between HDL cholesterol levels and incidence of cardiovascular events. Several functional activities associated with HDL and apoA-I are believed to promote these beneficial effects, including both facilitation of reverse cholesterol transport and additional cardioprotective anti-oxidant and anti-inflammatory functions (Navab, M., et al., 2000, *Journal of Lipid Research*. 41:1481-1494, Van Lenten, B. J., et al., 2001, *Trends in Cardiovascular Medicine*. 11:155-161, Nofer, J. R., et al., 2002, *Atherosclerosis*. 161:1-16). A major determinant of plaque progression/regression rate is the balance between cholesterol uptake versus efflux pathways. Enhanced cholesterol efflux from arterial cells, such as with over-expression of human apoA-I in apoE deficient mice (Plump, A. S., et al., 1994, *Proceedings of the National Academy of Sciences of the United States of America*. 91:9607-9611), or infusions of recombinant apoA-I forms into subjects, reduces atherosclerotic lesion plaque volume (Nissen, S. E., et al., 2003, *JAMA*. 290:2292-2300). ABCA1 also participates in cholesterol efflux from cells, functioning as a major regulator of macrophage cholesterol efflux and HDL-mediated reverse cholesterol transport (Francis, G. A., et al., 1995, *Journal of Clinical Investigation*. 96:78-87, Brooks-Wilson, A., et al., 1999, *Nature Genetics*. 22:336-345, Bodzioch, M., et al., 1999, *Nature Genetics*. 22:347-351, Rust, S., et al., 1999, *Nature Genetics*. 22:352-355, Lawn, R. M., et al., 1999, *Journal of Clinical Investigation*. 104:R25-31). Up-regulation of ABCA1 in liver and macrophages of transgenic mice reduces diet-induced atherosclerosis (Singaraja, R. R., et al., 2002, *Journal of Clinical Investigation*. 110:35-42), and bone marrow transplantation studies demonstrate that the selective inactivation of ABCA1 in macrophages markedly increases atherosclerosis and foam cell accumulation in apoE(−/−) mice (Aiello, R. J., et al., 2002, *Arteriosclerosis, Thrombosis & Vascular Biology*. 22:630-637).

While initial studies with MPO-KO mice demonstrated a modest increase, rather than an anticipated decrease, in lesions development, these studies also revealed significant species differences between rodents and humans with respect to MPO (Brennan, M. L., et al., 2001, *J. Clin. Invest*. 107:419-30). Specifically, while MPO and its oxidation products are enriched in human atheroma, neither MPO nor its specific oxidation products could be demonstrated in mouse aortic lesions, suggesting that human clinical studies were required to determine the role of MPO in human atherosclerosis. The past several years have witnessed an increasing number of clinical and genetic studies in humans supporting a role for MPO in atherogenesis. In an analysis of nearly 100 individuals with MPO deficiency, subjects lacking functional peroxidase activity were shown to have a significantly reduced rate of cardiovascular events (Kutter D, et al., 2000, *Acta Haematol*. 104:10-5). In several independent genetic studies, a functional polymorphism in the promoter region of the MPO gene that leads to decreased expression has been associated with significant cardioprotective effects in subjects harboring the mutation (Nikpoor B, et al., 2001, *Am. Heart J*. 142:336-39, Pecoits-Filho R, et al., 2003, *Kidney Int. Suppl*. 84:172-176, Asselbergs F W, et al., 2004, *Am J. Med*. 116:429-430). Plasma, serum and leukocyte MPO levels have now been associated with angiographic evidence of coronary artery disease (Zhang, R., et al., 2001, *JAMA*. 286:2136-2142), incident risk of myocardial infarction, death, and need for revascularization (Brennan, M. L., et al., 2003, *New England Journal of Medicine*. 349:1595-1604, Baldus, S., et al., 2003, *Circulation*. 108:1440-1445), and enhanced endothelial dysfunction (Vita J A, et al., 2004, *Circulation* (in press)). The observed selective targeting of apoA-I for oxidative modification by MPO in vivo, and the apparent accompanying functional impairment in ABCA1-dependent cholesterol efflux function of the lipoprotein, both serve to further suggest that development of an inhibitor of MPO may be of clinical benefit. Alternatively, it is tempting to speculate that the potential apoA-I binding site for MPO identified through the hydrogen/deuterium exchange studies may represent a unique therapeutic target for disrupting aberrant MPO activity in CVD subjects without interfering in needed actions of the enzyme such as innate host defenses.

Example 2

Figure 9:
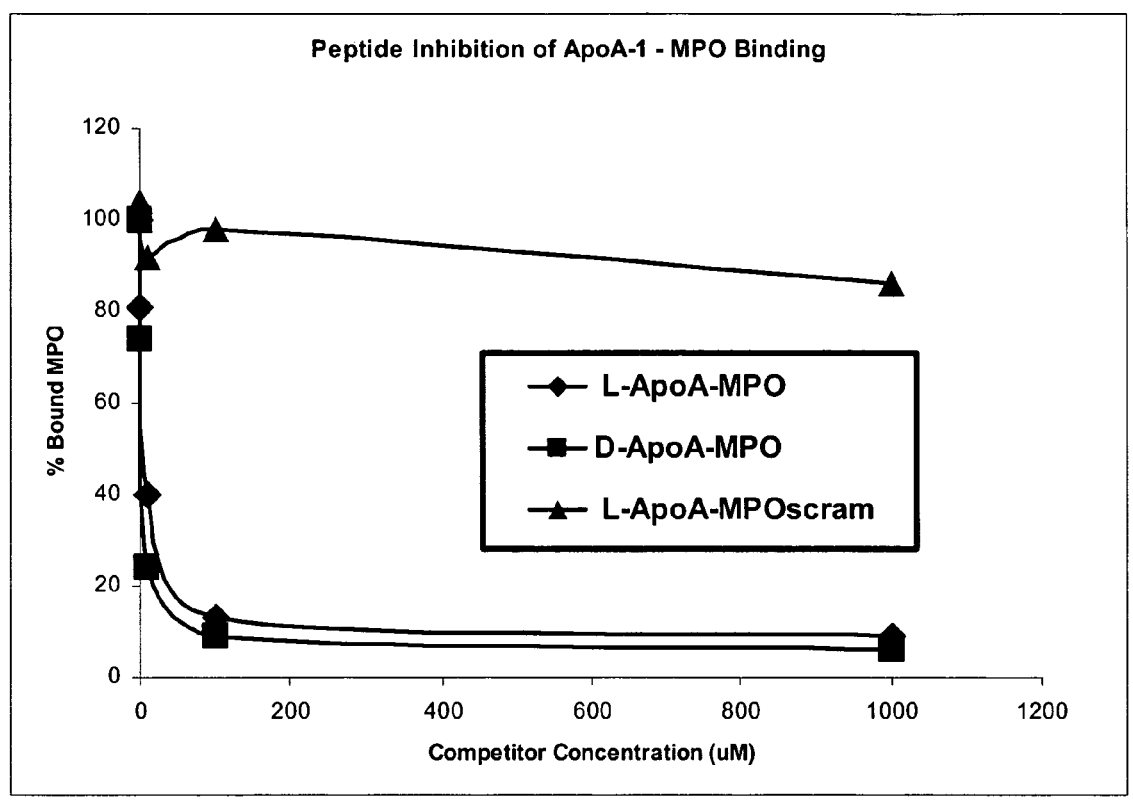
FIG. 9 Effect on binding of MPO to apoA1 by a peptide comprising L amino acids and the sequence AEYHAKATE-HLSTL, SEQ ID NO:2, D amino acids and the sequence set forth in SEQ ID NO: 2, or L amino acids and the sequence KHETHSLAYAAET, SEQ ID NO:4.

Effect of a Peptide Comprising L Amino Acids and the Sequence and a Retro-Inverso Isoform Thereof on MPO Binding to HDL Isolated human MPO was bound to the wells in a 96 well plate and then the binding of human apoA-1 to the MPO was determined in the presence of a peptide comprising the sequence N—Ac-(L) AEYHAKATEHLSTL, SEQ ID NO: 2 (also known as the L-ApoA-MPO peptide), a secquence comprising SEQ ID NO: 2 and D amino acids, also known as the D-apoA-MPO peptide, and a peptide comprising the sequence, N—Ac (L) KHETHSLAYAAET, SEQ ID NO: 4. As shown in FIG. 9, the L and D peptides comprising SEQ ID NO: 2 inhibited binding of apo A-1 to MPO; while the L peptide comprising SEQ ID NO: 4, a sequence unrelated to the MPO binding site of apoA-1 had no effect on MPO-apoA-1 binding.

What is claimed is:

1. A method of treating a subject who has, is at risk of having, or is at risk of developing a cardiovascular disease, comprising:
   administering to the subject an efficacious amount of an agent that inhibits binding of myeloperoxidase (MPO) to the MPO binding site of apolipoprotein A-1 (apoA-1), wherein the MPO binding site is located in the helix 8 domain of apoA1, and wherein the agent is one or more of the following:
   (a) a purified peptide that consists of the helix 8 domain of apo A-1 or a portion thereof, wherein said portion is at least 5 amino acids in length and comprises at least 4 consecutive amino acids in SEQ ID NO:2;
   (b) a purified peptide that is from 4 to 14 amino acids in length, wherein the sequence of the peptide that is 4 amino acids in length is identical to 4 consecutive amino acids in the sequence, AEYHAKATEHLSTL, SEQ ID NO:2, wherein the sequence of the peptide that is 5 amino acids in length is identical to 5 consecutive amino acids in SEQ ID NO:2, wherein the sequence of the peptide that is 6 amino acids in length is identical to 6 consecutive amino acids in SEQ ID NO:2, wherein the sequence of the peptide that is 7 amino acids in length is identical to 7 consecutive amino acids in SEQ ID NO:2, wherein the sequence of the peptide that is 8 amino acids in length is identical to 8 consecutive amino acids in SEQ ID NO:2, wherein the sequence of the peptide that is 9 amino acids in length is identical to 9 consecutive amino acids in SEQ ID NO:2, wherein the sequence of the peptide that is 10 amino acids in length is identical to 10 consecutive amino acids in SEQ ID NO:2, wherein the sequence of the peptide that is 11 amino acids in length is identical to 11 consecutive amino acids in SEQ ID NO:2, wherein the sequence of the peptide that is 12 amino acids in length is identical to 12 consecutive amino acids in SEQ ID NO:2, wherein the sequence of the peptide that is 13 amino acids in length is identical to 13 consecutive amino acids in SEQ ID NO:2, wherein the sequence of the peptide that is 14 amino acids in length is identical to SEQ ID NO:2, and wherein the peptide comprises L amino acids, D amino acids, or both;
   (c) a purified peptide that is from 4 to 14 amino acids in length, wherein the sequence of the peptide that is 4 amino acids in length has a sequence that is identical to 4 consecutive amino acids in LTSLHETAKAHYEA, SEQ ID NO: 3, wherein the sequence of the peptide that is 5 amino acids in length is identical to 5 consecutive amino acids in SEQ ID NO:3, wherein the sequence of the peptide that is 6 amino acids in length is identical to 6 consecutive amino acids in SEQ ID NO:3, wherein the sequence of the peptide that is 7 amino acids in length is identical to 7 consecutive amino acids in SEQ ID NO:3, wherein the sequence of the peptide that is 8 amino acids in length is identical to 8 consecutive amino acids in SEQ ID NO:3, wherein the sequence of the peptide that is 9 amino acids in length is identical to 9 consecutive amino acids in SEQ ID NO:3, wherein the sequence of the peptide that is 10 amino acids in length is identical to 10 consecutive amino acids in SEQ ID NO:3 wherein the sequence of the peptide that is 11 amino acids in length is identical to 11 consecutive amino acids in SEQ ID NO:3, wherein the sequence of the peptide that is 12 amino acids in length is identical to 12 consecutive amino acids in SEQ ID NO:3, wherein the sequence of the peptide that is 13 amino acids in length is identical to 13 consecutive amino acids in SEQ ID NO:3, wherein the peptide that is 14 amino acids is identical to SEQ ID NO:3, and wherein the peptide comprises D amino acids;
   (d) a modified version of the peptide of (a), (b), or (c), wherein the modified version of the peptide has a sequence at least 80% identical to the sequence of the peptide of (a), (b), or (c),
   wherein the modified version of the peptide does not have amino acids attached to the amino terminus or the carboxyl terminus of the peptide of (a), (b) or (c), and
   wherein the modified version of said peptide comprises one or more modifications selected from
   i) a deletion, substitution, and/or insertion of one or more amino acids in the sequence of a peptide of (a), (b), or (c);
   ii) non-sequence modifications;
   iii) one or more modified carboxylic acid groups, one or more modified amino groups, one or more modified hydroxyl groups, one or more modified phenyl groups, one or more modified methylene groups, and/or one or more modified thiol groups and/or wherein said modified version of the peptide of (a), (b), (c), is cyclized, and/or wherein one or more R groups on the constituent amino acids and/or the terminal amino acids of said modified version of the peptide of (a), (b), or (c) is blocked by a protecting group; and
   (iv) a substitution of one or more non-naturally occurring amino acids in the sequence of a peptide of (a), (b), or (c); or
   (e) a peptide mimetic of a peptide of (a), (b), or (c) wherein said peptide mimetic is 4-14 residues in length, said residues being an amino acid or a modified amino acid that results in one or more of the peptide linkages in the peptide of (a), (b), or (c) being replaced with a non-peptide linkage.

2. The method of claim 1, wherein the agent is an isolated or purified modified version of a peptide of (a), (b), or (c) as set forth in section (d) of claim 1, and wherein said modified version of said peptide has a sequence that is at least 90% identical to a 4 to 14 amino acid sequence in the sequence, AEYHAKATEHLSTL, SEQ ID NO:2 or in the sequence LTSLHETAKAHYEA, SEQ ID NO: 3.

3. The method of claim 1, wherein the agent is a peptide mimetic as set forth in section (e) of claim 1 and wherein one or more of the peptide linkages is replaced with linkage selected from the group consisting of: —CH₂NH—, —CH₂S —, —CH₂CH₂—, —CH=CH—(cis and trans), —COCH₂—, —CH(OH) CH₂—, and —CH₂SO—.

4. The method of claim 1, wherein the subject is a human subject and has exhibited one or more complications of cardiovascular disease or has been diagnosed as having cardiovascular disease.

5. The method of claim 1, wherein the subject is a human subject that has at least one risk factor for cardiovascular disease.

6. The method of claim 1, wherein the subject is an apparently healthy subject who is a non-smoker.

7. The method of claim 1, wherein the agent is a peptide that is chemically bonded to another group selected from a carbohydrate chain, polyethylene glycol, a heterologous peptide, and a blocking group.

8. A method of treating a subject who has, is at risk of having, or is at risk of developing a cardiovascular disease, comprising:
   administering to the subject a pharmaceutical composition comprising one or more of the following:
   (a) a purified peptide that is from 4 to 14 amino acids in length, wherein the sequence of the peptide that is 4 amino acids in length is identical to 4 consecutive amino acids in the sequence, AEYHAKATEHLSTL, SEQ ID NO:2, wherein the sequence of the peptide that is 5 amino acids in length is identical to 5 consecutive amino acids in SEQ ID NO:2, wherein the sequence of the peptide that is 6 amino acids in length is identical to 6 consecutive amino acids in SEQ ID NO:2, wherein the sequence of the peptide that is 7 amino acids in length is identical to 7 consecutive amino acids in SEQ ID NO:2, wherein the sequence of the peptide that is 8 amino acids in length is identical to 8 consecutive amino acids in SEQ ID NO:2, wherein the sequence of the peptide that is 9 amino acids in length is identical to 9 consecutive amino acids in SEQ ID NO:2, wherein the sequence of the peptide that is 10 amino acids in length is identical to 10 consecutive amino acids in SEQ ID NO:2, wherein the sequence of the peptide that is 11 amino acids in length is identical to 11 consecutive amino acids in SEQ ID NO:2, wherein the sequence of the peptide that is 12 amino acids in length is identical to 12 consecutive amino acids in SEQ ID NO:2, wherein the sequence of the peptide that is 13 amino acids in length is identical to 13 consecutive amino acids in SEQ ID NO:2, wherein the sequence of the peptide that is 14 amino acids in length is identical to SEQ ID NO:2, and wherein the peptide comprises L amino acids, D amino acids, or both;
   (b) a purified peptide that is from 4 to 14 amino acids in length, wherein the sequence of the peptide that is 4 amino acids in length has a sequence that is identical to 4 consecutive amino acids in LTSLHETAKAHYEA, SEQ ID NO: 3, wherein the sequence of the peptide that is 5 amino acids in length is identical to 5 consecutive amino acids in SEQ ID NO:3, wherein the sequence of the peptide that is 6 amino acids in length is identical to 6 consecutive amino acids in SEQ ID NO:3, wherein the sequence of the peptide that is 7 amino acids in length is identical to 7 consecutive amino acids in SEQ ID NO:3, wherein the sequence of the peptide that is 8 amino acids in length is identical to 8 consecutive amino acids in SEQ ID NO:3, wherein the sequence of the peptide that is 9 amino acids in length is identical to 9 consecutive amino acids in SEQ ID NO:3, wherein the sequence of the peptide that is 10 amino acids in length is identical to 10 consecutive amino acids in SEQ ID NO:3 wherein the sequence of the peptide that is 11 amino acids in length is identical to 11 consecutive amino acids in SEQ ID NO:3, wherein the sequence of the peptide that is 12 amino acids in length is identical to 12 consecutive amino acids in SEQ ID NO:3, wherein the sequence of the peptide that is 13 amino acids in length is identical to 13 consecutive amino acids in SEQ ID NO:3, wherein the peptide that is 14 amino acids is identical to SEQ ID NO:3, and wherein the peptide comprises D amino acids;
   (c) a modified version of the peptide of (a) or (b), provided that the modified version of the peptide does not have one or more amino acids attached to the amino terminus or carboxy terminus of a peptide of (a) or (b), wherein the modified version of the peptide has a sequence at least 80% identical to the sequence of a peptide of (a) or (b), and wherein said modified version of said peptide comprises one or more modifications selected from
      i) a deletion, substitution, and/or insertion of one or more amino acids in the sequence of a peptide of (a) or (b);
      ii) non-sequence modifications;
      iii) one or more modified carboxylic acid groups, one or more modified amino groups, one or more modified hydroxyl groups, one or more modified phenyl groups, one or more modified methylene groups, and/or one or more modified thiol groups and/or wherein said modified version of the peptide of (a) or (b) is cyclized, and/or wherein one or more R groups on the constituent amino acids and/or the terminal amino acids of said modified version of the peptide of (a) or (b) is blocked by a protecting group; and
      iv) a substitution of one or more non-naturally occurring amino acids in the sequence of a peptide of (a) or (b); or
   (d) a peptide mimetic of a peptide of (a), or (b), wherein said peptide mimetic is 4-14 residues in length, said residues being an amino acid or a modified amino acid that results in one or more of the peptide linkages in the peptide of (a) or (b) being replaced with a non-peptide linkage.

9. The method of claim 8, further comprising administering to the subject a therapeutic agent chosen from an anti-inflammatory agent, an antithrombotic agent, an antiplatelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, or combinations thereof.

10. A method of treating a subject who has, is at risk of having, or is at risk of developing a cardiovascular disease, comprising:
   administering to the subject a pharmaceutical composition comprising one or more of the following:
   (a) a purified peptide that is from 5 to 14 amino acids in length, wherein the sequence of the peptide that is 5 amino acids in length is identical to 5 consecutive amino acids in SEQ ID NO:2, wherein the sequence of the peptide that is 6 amino acids in length is identical to 6 consecutive amino acids in SEQ ID NO:2, wherein the sequence of the peptide that is 7 amino acids in length is identical to 7 consecutive amino acids in SEQ ID NO:2, wherein the sequence of the peptide that is 8 amino acids in length is identical to 8 consecutive amino acids in SEQ ID NO:2, wherein the sequence of the peptide that is 9 amino acids in length is identical to 9 consecutive amino acids in SEQ ID NO:2, wherein the sequence of the peptide that is 10 amino acids in length is identical to 10 consecutive amino acids in SEQ ID NO:2, wherein the sequence of the peptide that is 11 amino acids in length is identical to 11 consecutive amino acids in SEQ ID NO:2, wherein the sequence of the peptide that is 12 amino acids in length is identical to 12 consecutive amino acids in SEQ ID NO:2, wherein the sequence of the peptide that is 13 amino acids in length is identical to 13 consecutive amino acids in SEQ ID NO:2, wherein the sequence of the peptide that is 14 amino acids in length is identical to SEQ ID NO:2, and wherein the peptide comprises L amino acids, D amino acids, or both, or (b) a purified peptide that is from 5 to 14 amino acids in length, wherein the sequence of the peptide that is 5 amino acids in length is identical to 5 consecutive amino acids in SEQ ID NO:3, wherein the sequence of the peptide that is 6 amino acids in length is identical to 6 consecutive amino acids in SEQ ID NO:3, wherein the sequence of the peptide that is 7 amino acids in length is identical to 7 consecutive amino acids in SEQ ID NO:3, wherein the sequence of the peptide that is 8 amino acids in length is identical to 8 consecutive amino acids in SEQ ID NO:3, wherein the sequence of the peptide that is 9 amino acids in length is identical to 9 consecutive amino acids in SEQ ID NO:3, wherein the sequence of the peptide that is 10 amino acids in length is identical to 10 consecutive amino acids in SEQ ID NO:3 wherein the sequence of the peptide that is 11 amino acids in length is identical to 11 consecutive amino acids in SEQ ID NO:3, wherein the sequence of the peptide that is 12 amino acids in length is identical to 12 consecutive amino acids in SEQ ID NO:3, wherein the sequence of the peptide that is 13 amino acids in length is identical to 13 consecutive amino acids in SEQ ID NO:3, wherein the peptide that is 14 amino acids is identical to SEQ ID NO:3, and wherein the peptide comprises D amino acids;

wherein said peptide is optionally modified with non-sequence modifications or wherein one or more R groups on the constituent amino acids and/or the terminal amino acids of said peptide is optionally blocked by a protecting group.

11. The method of claim 1, further comprising administering to the subject a therapeutic agent chosen from an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, or combinations thereof.

* * * * *

UNITED STATES PATENT AND TRADEMARK OFFICE
CERTIFICATE OF CORRECTION

| | |
|---|---|
| PATENT NO. | : 7,378,396 B2 |
| APPLICATION NO. | : 11/198005 |
| DATED | : May 27, 2008 |
| INVENTOR(S) | : Stanley L. Hazen and Marc S. Penn |

It is certified that error appears in the above-identified patent and that said Letters Patent is hereby corrected as shown below:

Column 7, line 40, after "14" please insert -- consecutive --.

Signed and Sealed this

Twenty-ninth Day of July, 2008

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80
```

```
Gly Leu Arg Gln Glu Met Ser Lys Asp Leu Glu Val Lys Ala Lys
                 85                  90                  95

Val Gln Pro Tyr Leu Asp Asp Phe Gln Lys Lys Trp Gln Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

SEQ ID NO 2
LENGTH: 14
TYPE: PRT
ORGANISM: Homo sapiens

SEQUENCE: 2

Ala Glu Tyr His Ala Lys Ala Thr Glu His Leu Ser Thr Leu
 1               5                  10

<210> SEQ ID NO 3
<211> LENGTH: 14
<212> TYPE: PRT
<213> ORGANISM: Homo sapiens

<400> SEQUENCE: 3

Leu Thr Ser Leu His Glu Thr Ala Lys Ala His Tyr Glu Ala
 1               5                  10

<210> SEQ ID NO 4
<211> LENGTH: 13
<212> TYPE: PRT
<213> ORGANISM: Homo sapiens

<400> SEQUENCE: 4

Lys His Glu Thr His Ser Leu Ala Tyr Ala Ala Glu Thr
 1               5                  10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:  Synthetic
      peptide
<220> FEATURE:
<221> NAME/KEY: MOD_RES
<222> LOCATION: (3)
<223> OTHER INFORMATION: NO2-Tyr
<220> FEATURE:
<221> NAME/KEY: MOD_RES
```

-continued

```
<222> LOCATION: (7)
<223> OTHER INFORMATION: NO2-Tyr

<400> SEQUENCE: 5

Cys Gly Tyr Gly Gly Gly Tyr Gly
 1               5
```